US008058632B2

(12) United States Patent
Balestracci et al.

(10) Patent No.: US 8,058,632 B2
(45) Date of Patent: Nov. 15, 2011

(54) CONTAINERS FOR PHARMACEUTICALS, PARTICULARLY FOR USE IN RADIOISOTOPE GENERATORS

(75) Inventors: Ernest Balestracci, Iselin, NJ (US); James A. Melchore, Jr., Bloomsbury, NJ (US); Jo Anna Monteferrante, Flemington, NJ (US); Irene Kucharewicz Ropiak, Lawrenceville, NJ (US); Ernst Schramm, Milltown, NJ (US); Julius P. Zodda, Mercerville, NJ (US); Charles R. Quirico, Warren, NJ (US)

(73) Assignee: Bracco Diagnostics, Inc., Princeton, NJ (US)

( * ) Notice: Subject to any disclaimer, the term of this patent is extended or adjusted under 35 U.S.C. 154(b) by 179 days.

(21) Appl. No.: 12/358,711

(22) Filed: Jan. 23, 2009

(65) Prior Publication Data

US 2009/0129989 A1    May 21, 2009

Related U.S. Application Data

(62) Division of application No. 10/597,456, filed on Jan. 17, 2007.

(60) Provisional application No. PCT/US2005/030796, filed on Aug. 30, 2005, now Pat. No. 7,504,646, provisional application No. 60/605,481, filed on Aug. 30, 2004.

(51) Int. Cl.
*G21F 5/00*    (2006.01)

(52) U.S. Cl. ............... 250/507.1; 250/505.1; 250/506.1

(58) Field of Classification Search .................. None
See application file for complete search history.

(56) References Cited

U.S. PATENT DOCUMENTS

| | | | | |
|---|---|---|---|---|
| 3,710,118 A | * | 1/1973 | Holgate et al. | 250/432 R |
| 3,774,035 A | | 11/1973 | Litt | |
| 3,920,995 A | * | 11/1975 | Czaplinski et al. | 250/432 R |
| 3,953,567 A | | 4/1976 | Grant et al. | |
| 3,970,583 A | | 7/1976 | Panek-Finda | |
| 4,041,317 A | | 8/1977 | Morcos | |
| 4,294,250 A | | 10/1981 | Dennehey | |
| 4,400,358 A | | 8/1983 | Neirinckx | |
| 4,406,877 A | | 9/1983 | Neirinckx et al. | |
| 4,447,230 A | * | 5/1984 | Gula et al. | 604/122 |
| 4,562,829 A | * | 1/1986 | Bergner | 600/4 |
| 4,585,009 A | * | 4/1986 | Barker et al. | 600/432 |
| 4,585,941 A | * | 4/1986 | Bergner | 250/363.02 |
| 4,745,907 A | | 5/1988 | Russel, Jr. et al. | |

(Continued)

FOREIGN PATENT DOCUMENTS

EP    1293228    3/2003

(Continued)

OTHER PUBLICATIONS

European Search Report dated Jan. 21, 2011 for European Application No. 10196142.3, 6 pages.

(Continued)

*Primary Examiner* — Robert Kim
*Assistant Examiner* — Andrew Smyth
(74) *Attorney, Agent, or Firm* — Fredrikson & Byron, P.A.

(57) ABSTRACT

The invention is directed to improved containers for pharmaceuticals and any tubing and tubing connectors associated therewith, particularly containers for pharmaceuticals which are irradiated, heated or otherwise subjected to increased pressure. In a preferred embodiment, the invention is directed to an improved container for use in a radioisotope generator, such as a rubidium-82 generator.

14 Claims, 15 Drawing Sheets

U.S. PATENT DOCUMENTS

| | | | |
|---|---|---|---|
| 4,755,679 | A | 7/1988 | Wong |
| 4,876,073 | A | 10/1989 | Issachar et al. |
| 4,923,088 | A * | 5/1990 | Tanaka et al. ............... 220/23.87 |
| 4,929,243 | A | 5/1990 | Koch et al. |
| 4,968,308 | A | 11/1990 | Herlitze et al. |
| 5,047,021 | A | 9/1991 | Utterberg |
| 5,109,160 | A | 4/1992 | Evers |
| 5,391,139 | A | 2/1995 | Edmundson |
| 5,397,902 | A * | 3/1995 | Castner et al. .......... 250/432 PD |
| 5,485,831 | A | 1/1996 | Holdsworth et al. |
| 5,497,951 | A | 3/1996 | Watajima |
| 5,586,153 | A | 12/1996 | Alvord |
| 5,611,576 | A | 3/1997 | Guala |
| 5,922,304 | A * | 7/1999 | Unger ............................. 424/9.3 |
| 6,140,649 | A | 10/2000 | Lonn |
| 6,235,264 | B1 | 5/2001 | Uzgiris |
| 6,254,552 | B1 * | 7/2001 | Lewis et al. ........................ 600/3 |
| 6,315,981 | B1 * | 11/2001 | Unger ........................ 424/9.323 |
| 6,373,068 | B1 * | 4/2002 | Nijsen et al. ............ 250/432 PD |
| 6,488,666 | B1 * | 12/2002 | Geist ............................. 604/263 |
| 6,565,550 | B1 | 5/2003 | Klein et al. |
| RE38,189 | E * | 7/2003 | Walker et al. ................. 604/207 |
| 6,612,624 | B1 * | 9/2003 | Segal et al. ................... 285/330 |
| 6,638,263 | B1 | 10/2003 | Theeuwes et al. |
| 6,656,157 | B1 * | 12/2003 | Duchon et al. ................ 604/131 |
| 6,767,319 | B2 * | 7/2004 | Reilly et al. ....................... 600/5 |
| 6,843,513 | B2 | 1/2005 | Guala |
| 6,870,175 | B2 * | 3/2005 | Dell et al. .................. 250/506.1 |
| 6,908,598 | B2 | 6/2005 | Sylvester |
| 7,023,000 | B2 | 4/2006 | Zyuzin |
| 2002/0147429 | A1 | 10/2002 | Cowan |
| 2004/0193145 | A1 | 9/2004 | Raudabough et al. |
| 2004/0260143 | A1 | 12/2004 | Reilly et al. |
| 2005/0116186 | A1 | 6/2005 | Weisner et al. |
| 2005/0218347 | A1 | 10/2005 | Williamson et al. |
| 2005/0238576 | A1 | 10/2005 | Dell et al. |
| 2005/0273007 | A1 | 12/2005 | Burbar |
| 2006/0045229 | A1 | 3/2006 | Balestracci |
| 2006/0159621 | A1 | 7/2006 | Barrett |
| 2006/0217343 | A1 | 9/2006 | Rieger et al. |

FOREIGN PATENT DOCUMENTS

| | | |
|---|---|---|
| FR | 2218622 A1 | 9/1974 |
| GB | 1473236 A | 5/1977 |
| GB | 2067343 A | 7/1981 |
| JP | 8-238297 A | 9/1996 |
| WO | 97/26941 | 7/1997 |
| WO | 0033322 A1 | 6/2000 |
| WO | 2006026603 A2 | 3/2006 |

OTHER PUBLICATIONS

European Search Report dated Jan. 30, 2009, 10 pages.

* cited by examiner

CONTAINERS FOR PHARMACEUTICALS, PARTICULARLY FOR USE IN RADIOISOTOPE GENERATORS

This is a divisional application of U.S. application Ser. No. 10/597,456, filed Jan. 17, 2007, now allowed, which claims priority from PCT Application No. PCT/US2005/030796, filed Aug. 30, 2005, which claims priority from provisional U.S. Application No. 60/605,481, filed Aug. 30, 2004.

TECHNICAL FIELD OF THE INVENTION

The invention is directed to improved containers for pharmaceuticals and the tubing and tubing connectors associated therewith, particularly containers for pharmaceuticals which are heated, irradiated or otherwise subjected to increased pressure. In a preferred embodiment, the invention is directed to an improved container for use in a radioisotope generator. Specifically, the designs and materials of the column container and its closure and associated tubing and tubing connectors have been improved.

SUMMARY OF THE INVENTION

The invention includes improved pharmaceutical containers, particularly improved containers for pharmaceuticals that are subjected to increased pressure (such as by heating or other means) and/or are subjected to radioactivity. In a preferred embodiment, the invention is directed to an improved container, also called a column, for use in a radioisotope generator. In an especially preferred embodiment, the improved column is for use with rubidium-82 generator such as those disclosed in U.S. Pat. Nos. 3,953,567; 4,400,358; 4,406,877; 4,562,829; 4,585,009; 4,585,941; and 5,497,951, incorporated herein by reference in their entirety. In a particularly preferred embodiment, the improved column is used in a rubidium-82 generator such as that sold under the trade name CardioGen®.

The improved pharmaceutical container of the invention includes an improved seal and crimping process, as well as changes to the design of the stopper and the container to prevent blockages and improve consistency in packing and closing the container, which improves flow rate and elution from the column.

Further improvements include constructing the container and stopper out of radiation resistant or tolerant materials. In addition, flexible tubing used with the container is made of a radiation resistant or tolerant material, and the Luer locks used to fasten the flexible tubing to the container is made of a radiation resistant or tolerant material and is further improved to insure a tight, secure lock which will not inadvertently loosen or disconnect.

Specifically, the improved container has a new, stronger seal which is used to crimp the stopper in a pharmaceutical container and particularly, which is used to seal a radioisotope generator column/stopper assembly system, such as the CardioGen® system. This improved seal prevents leakage, even at increased pressure, and reduces ballooning of the rubber stopper material. The seal has a configuration similar to one of those shown in FIG. 5B through FIG. 5F and FIGS. 6A and 6B and is made of any suitably strong material including metal or plastic. A pneumatically operated automatic or semi-automatic crimper, set at optimized pressure, is preferably used to crimp the seal during assembly of a pharmaceutical container such as a radioisotope generator column/stopper assembly system. The invention includes identification of optimized crimping pressure(s) for crimping the seal (regardless of material) to a pharmaceutical container such as a glass or plastic vial or column and thus securing in place a rubber closure(s) when using an automatic crimping system and/or manual crimping.

The stopper which is crimped into place is also improved. Specifically, it is made of a material which is radiation resistant or tolerant, is resistant to ballooning and can withstand the pressure at which the container operates. Additionally, the configuration and placement of the stopper at the bottom of the column reduces the "dead volume"-space where non-radioactive, decayed eluate could mix with (and dilute) fresh, radioactive eluate, reducing the efficacy of the eluent.

The improved pharmaceutical container also includes improvements to the design which improve its packing/assembly and thus ensure specified flow of eluent through the container.

These improvements are illustrated in the context of a radioisotope generator column container. Flow rate of the eluent through the column could be partially or completely blocked if the stopper blocks the outlet arm of the column. As shown in FIGS. 1A-1G, the outlet arm of the container of the invention has been repositioned slightly and a small piece of plastic removed from the inside edge of the column to create a recess or notch where the outlet arm enters the column lumen to prevent a stopper from blocking flow. See FIG. 4. A small reinforcement piece of resin is added to the outside of the column between the outlet arm and column body to provide additional strength.

Another improvement in the containers of the invention addresses consistency of assembly and packing of the containers. In prior columns for a radioisotope generator, a plastic basket or spacer was supplied separately and was placed on the top of the column packing before the seal was inserted and the seal crimped into place. In these prior columns, placement of the baskets or spacers, which hold the column packing in place, could vary significantly, potentially creating some problems with consistency in packing. In the improved columns, two small orientation knobs have been added to the outside of the top basket/spacer and the orientation knobs are positioned 180° apart. These knobs fit into two small slots cut into the wall of the column. This combination eliminates the potential variability of manual alignment and depth placement of the basket/spacer into the column and ensures a consistent fit every time. Critical to the function of the column is the alignment of the basket/spacer openings with the column inlet in the top arm. This prevents misalignment and consequent restricted flow and possible back pressure and also ensures consistent and timely out put of eluent to the patient.

Another improvement is to make the column assembly out of a radiation resistant or tolerant material, such as radiation resistant polypropylene. Likewise, the flexible tubing and Luer connector are made of radiation resistant or tolerant materials, such as radiation resistant polyvinylchloride. Furthermore, the Luer connector on the flexible tube and its counterpart Luer connector on the column assembly are configured to provide for a tight lock which will not leak and which will not loosen or inadvertently disconnect during use.

THE TECHNICAL PROBLEM AND ITS SOLUTION

The invention was designed to solve a number of technical problems experienced with prior art pharmaceutical containers.

1. Leakage From the Stopper/Column Interface

Leakage from the flange (or other area) of the seal of prior pharmaceutical containers such as column/stopper assembly systems was found to occur when the system was exposed to increasing pressure.

The new seal, consisting of a stronger material crimped at optimized crimping pressure, prevents leakage at the flange seal area even at increasing pressure.

2. Ballooning

Ballooning and/or burst of rubber materials (both before and after irradiation) through the center hole of current aluminum seals has been observed when they are subject to repeated pulsations of pressure cycling. The seals of the invention, which are stronger and are crimped at optimized pressure, reduce the likelihood of this problem. However, in a preferred embodiment the seal used in the improved container of the invention has a center hole of reduced size. For example, a seal with the configuration of those in FIG. 5B, FIG. 5C, FIG. 5E or FIGS. 6A and 6B may preferably be used. Due to the small center hole and strength of these seals, and crimping at optimized pressure, ballooning and/or burst of rubber materials is prevented. Consequently, pharmaceutical containers of the invention, and particularly column/stopper systems of the invention, can be exposed to much higher pressures during use of the system in the field.

In addition, the larger surface area of the crimp resulting from the reduction of the diameter of the center hole serves as additional support for the rubber closure and inhibits possible rupture as it is weakened over time due to the cumulative effect of exposure to radiation from the column or container content.

Also, the stopper is made of a radiation resistant or tolerant material. This also helps prevent ballooning and bursting.

3. Leakage Through Puncture Points

Leakage through puncture points has been observed in prior art pharmaceutical containers. Such leakage may be eliminated in containers of the invention through a combination of the stronger seal material, preferably a smaller center hole, and crimping at optimized pressure.

4. Splitting of the Seal

Splitting or tearing of current aluminum seals has been observed at pressures intended for use with a pharmaceutical container system (or pressures to which the system can potentially be exposed during intended usage in the field).

Due to the strength of the new seal material, no splitting or rupture of seal material is observed at pressures intended for use. For example, the seals on the columns of the invention do not split or rupture when used in, for example, a rubidium generator at intended pressures.

5. Inconsistent Manual Crimping Procedure

The manual crimping procedure commonly used with many prior container systems, including radioisotope column systems, is not always consistent and thus does not result in reproducible crimping pressures. Over-pressuring results in buckling and collapse of the skirt of the seal material. Under-pressuring results in a loose overseal. Use of the automatic or semi-automatic crimping procedure of the invention with compressed or pressurized air results in consistent/reproducible crimping pressures, and enables selection of optimized crimping pressures when crimping various seal materials.

6. Maintenance of Consistent Flow/Reduction of Back Pressure

In some prior pharmaceutical columns, flow rate of the eluent through the column could be partially or completely blocked because the stopper blocked the outlet arm of the column. The outlet arm of the container of the invention has been repositioned slightly and a small piece of plastic removed from the inside edge of the column to create a recess or notch where the outlet arm enters the column lumen to prevent a stopper from blocking flow. A small reinforcement piece of resin is added to the outside of the column between the outlet arm and column body to provide additional strength. The recessed outlet arm and notch near the bottom of the column body greatly reduces the chance of back pressure due to a stopper blocking the outlet arm.

7. Inconsistent Positioning Within Column

In a column for a radioisotope generator, a plastic basket or spacer is supplied separately and is placed on the top of the packed column before the seal or closure is inserted and the seal crimped into place. In prior columns, the baskets/spacers, which hold the column packing in place, were not easily positioned consistently both in terms of depth and orientation. In the improved columns of the invention, two small orientation knobs have been added to the outside of the top basket/spacer and these orientation knobs are positioned 180° apart. These knobs fit into two small slots cut into the wall of the column. This combination eliminates the potential variability of manual placement of the basket into the column, ensuring a consistent fit from generator to generator and reducing the variability in packing density associated with this manual process.

8. Degradation Due To Radiation

Many materials degrade when exposed to radiation. Degradation includes possible changes in color, loss of flexibility, increased brittleness and the leaching out of various substances from the materials. To avoid these potential problems, the column assembly, stopper, flexible tubing and Luer connectors are made out of radiation resistant or tolerant materials.

Frequently, when a material is said to be radiation resistant or tolerant, that means the material can withstand the amount of radiation used for sterilization, which is typically about 25 kGy. For the purposes of the present invention, however, a material is radiation resistant or tolerant when it can be exposed to about 145 kGy radiation and not degrade to the point where the functioning of the column assembly will be adversely affected.

9. Properly Closed Luer Locks

Luer locks are known in the art. However, it can be difficult to determine when a Luer lock has been sufficiently tightened to form a tight, non-leaking lock. Thus, one improvement is to provide for one or more tabs on each Luer connector. When the tabs achieve a certain orientation with respect to each other, for example when the tabs line up, such orientation means that the Luer lock has been sufficiently tightened.

Another potential difficulty with Luer locks is that they can come loose, i.e. disconnect, during use, which has the potential of causing a leak. To overcome this potential difficulty, the Luer connectors screw together and are each provided with one or more tabs. As the Luer connectors approach their fully tightened position, the tabs overlap. Further tightening causes the overlapping tabs to pass by each other, which can cause a clicking sound or sensation. When this occurs, the Luer lock is sufficiently tightened. Also, the Luer locks cannot become loose, e.g. unscrew, because the overlapping tabs will inhibit this action.

BRIEF DESCRIPTION OF THE FIGURES

FIG. 5A shows a prior art crimp seal.

DETAILED DESCRIPTION OF THE INVENTION

Figure 1A:
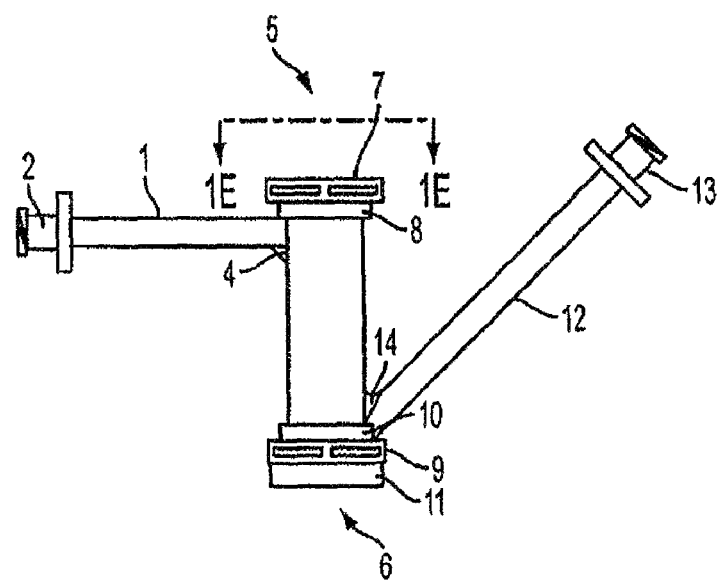
FIGS. 1A-1G show the inventive column assembly from different angles and cross sections.
Figure 1B:
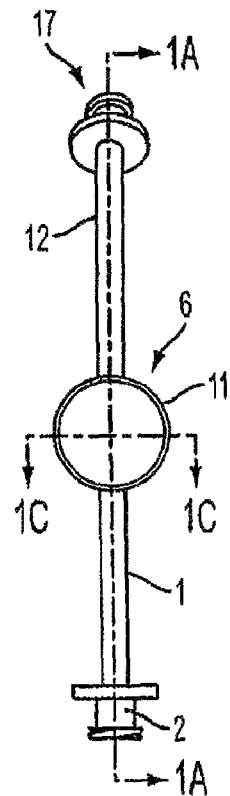

Referring now to FIG. 1, FIG. 1A shows a side view and FIG. 1B shows a bottom view of the inventive container (e.g., column assembly) of one embodiment of the invention. FIG. 1C is another side view of the inventive column assembly, cut along line A-A of FIG. 1B. FIG. 1D is detail B from FIG. 1C, at a scale of 3:1 compared to FIG. 1C. FIG. 1E is a top view of the inventive column assembly, cut along line E-E of FIG. 1A. FIG. 1F is another side view of the inventive column assembly, cut along line C-C of FIG. 1B. FIG. 1G is detail D of FIG. 1F, at a scale of 2:1 compared to FIG. 1F.

FIG. 1A has an inlet arm 1 which has an inlet arm female Luer cap 2 at its distal end. The proximal end of the inlet arm 1 attaches to the upper portion of a column 3. There is also an inlet arm support means 4 to support the inlet arm 1. The support means is preferably material which is added to support the inlet arm 1. Preferably, this material is the same material used to construct the column assembly. As shown, the inlet arm support means 4 is a triangular shaped member attached to the inlet arm 1 and the column 3, although the shape of the support is not limited to a triangle. It can be square, a bar passing from the inlet arm 1 to the column 3, or any other suitable shape.

The column 3 has a top portion 5 and a bottom portion 6. The top portion 5 comprises a first top portion 7 and a second top portion 8. The first top portion 7 is on top of and has a diameter greater then the second top portion 8, which is on top of and has a greater diameter than the column 3.

The bottom portion 6 of the column 3 has a similar configuration. It has a first bottom portion 9 and a second bottom portion 10. The first bottom portion 9 sits below and has a greater diameter than the second bottom portion 10, which sits below and has a greater diameter than the column 3. Also shown is a bottom stopper 11.

An outlet arm 12 is attached to the bottom portion of the column 3. The distal end of the outlet arm 12 terminates in an outlet arm female Luer cap 13. There is also an outlet arm support means 14 to support the outlet arm 12. The support means is preferably material which is added to support the outlet arm 12. Preferably, this material is the same material used to construct the column assembly. As shown, the outlet arm support means 14 is a triangular shaped member which attaches to the column and the outlet arm 12, although the shape of the support is not limited to a triangle. It can be a square, a bar passing from the outlet arm 12 to the column 3, or any other suitable shape.

Figure 1C:
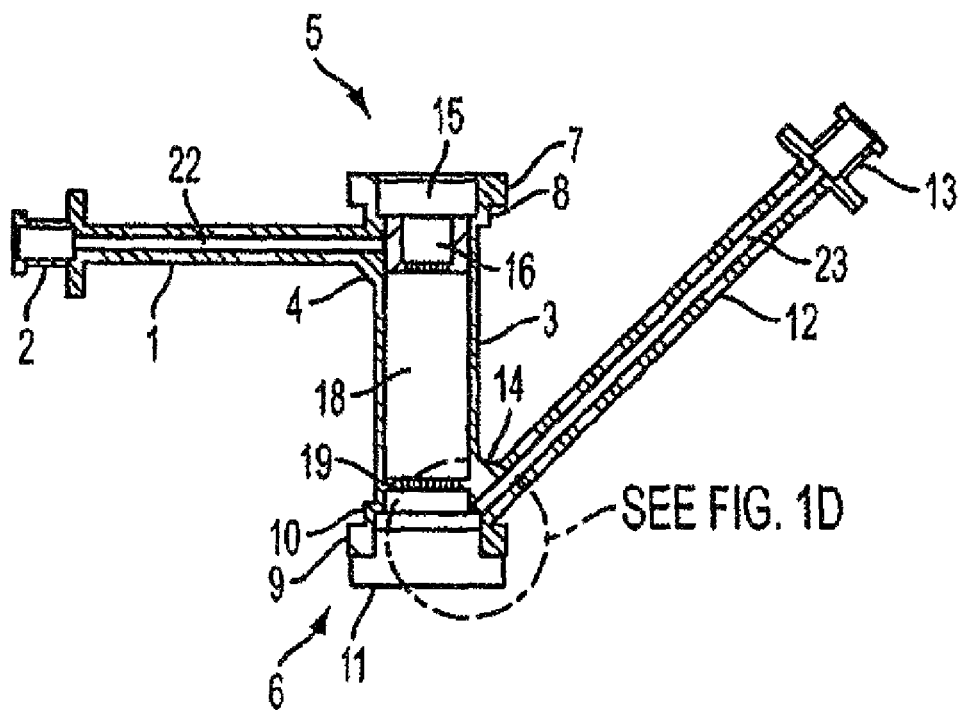

FIG. 1C shows a cross section of the inventive column assembly, cut through line A-A of FIG. 1B. As shown, the inlet arm 1, column 3 and outlet arm 12 are hollow.

Turning to the hollow interior or lumen of the column 3, it first defines a top stopper receptacle area 15. Below that and in communication with it is a top basket receptacle area 16. As shown in FIG. 1C, the top basket receptacle area 16 contains a top basket or spacer 17. Following that is a packing material containing area 18. Underneath the packing material containing area 18 is a bottom screen 19, followed by a bottom open area 20. Underneath the bottom open area 20 is a bottom stopper receptacle area 21.

FIG. 1C shows the bottom stopper 11 inserted into the bottom stopper receptacle area 21 of the column 3. Note that the bottom stopper 11 consumes most of the bottom stopper receptacle area 21. This minimizes the dead volume in the bottom stopper receptacle area 21. Minimization of the dead volume minimizes mixing of fresh, radioactive eluent with non-radioactive or decayed eluent, which could dilute the fresh eluent, thereby maintaining a narrow rubidium-82 bolus profile.

The inlet arm 1 and outlet arm 12 are each hollow, the hollow portions being 22 and 23 respectively, and are in communication with the hollow portion of the column 3. As shown in FIG. 1C, the hollow portion 22 of the inlet arm 1 is in communication with the top basket receptacle area 16.

Figure 1D:
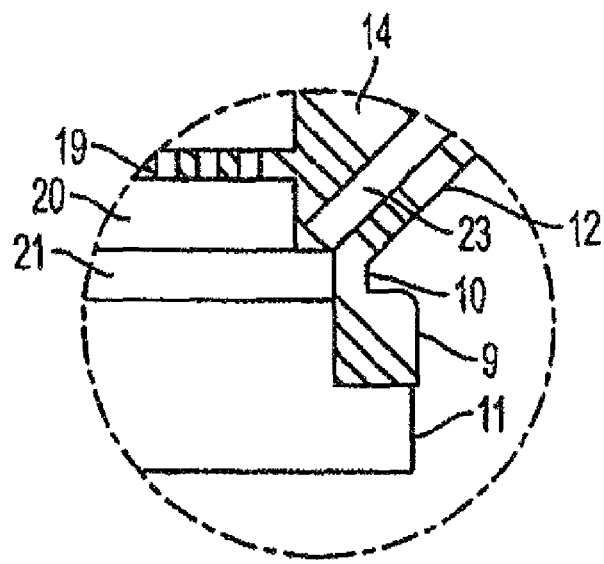

The intersection of the column 3 and the outflow arm 12 is shown in more detail in FIG. 1D. As shown therein, no portion of the outflow arm 12 extends into the hollow portion of the column 3, as was the case with certain prior art column assemblies. Also, the hollow portion 23 of the outflow arm 12 intersects the hollow portion of column 3 at the top of the bottom stopper receptacle area 21 or at about the place the bottom stopper receptacle area 21 and the bottom open area 20 intersect. This configuration, not found in prior art column assemblies, prevents the bottom stopper 11 from blocking the outflow arm 12.

In a preferred embodiment, an outflow notch 25 is formed where the hollow portion 23 of the outflow arm 12 intersects the hollow interior of the column 3, thus further preventing any blockage of the outflow arm 12 by the bottom stopper 11. This embodiment is shown in more detail in FIG. 4.

Figure 1E:
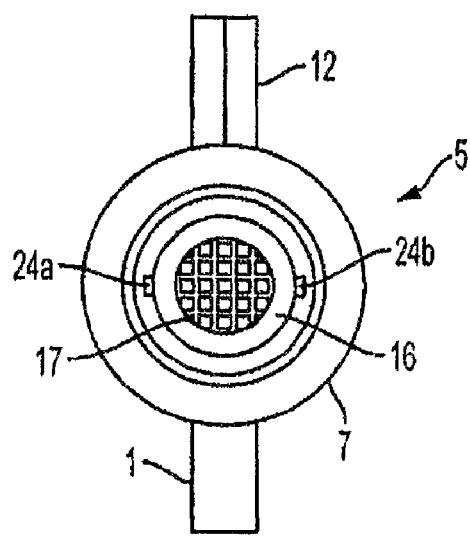

FIG. 1E is a top view of the inventive column assembly. Visible from this perspective are, for example, the top basket or spacer 17 and the top basket receptacle area 16. Also shown are notches 24a and 24b.

The notches 24a and 24b are made in the wall of the top basket receptacle area 16. As shown in FIG. 1E, they are 180 degrees opposed to each other. They are configured to cooperate with a pair of protrusions which appear on a top basket (discussed below with respect to FIGS. 3A-3D) such that the protrusions fit into notches 24a and 24b. This configuration insures proper placement of the top basket into the top basket receptacle area 16 so that the top basket is straight and at the correct depth. In prior art column assemblies, which lacked these notches and protrusions, it was possible to insert the top basket in such a manner that it was not straight and/or at the wrong depth, which adversely affected the function of the column assembly.

FIG. 1E shows two notches 24a and 24b 180° opposed to each other. It is understood that the present invention is not limited to this configuration. Rather, there can be 1, 3, 4, 5, 6 or more notches present in the wall of the top basket receptacle area 16 in any configuration, so long as these notches cooperate with protrusions on the top basket to insure its proper fit.

Figure 1F:
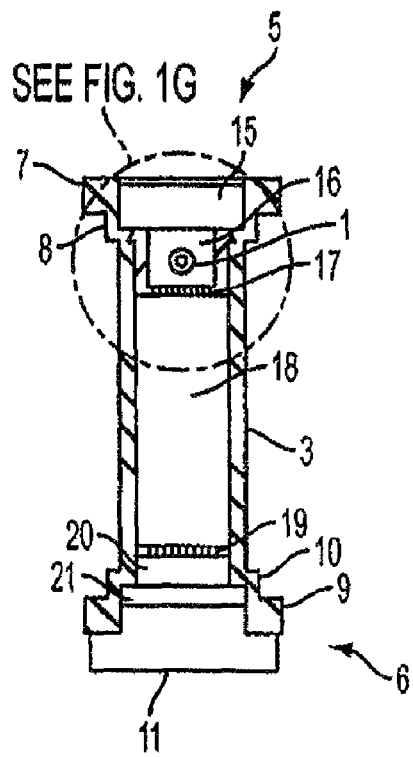
Figure 1G:
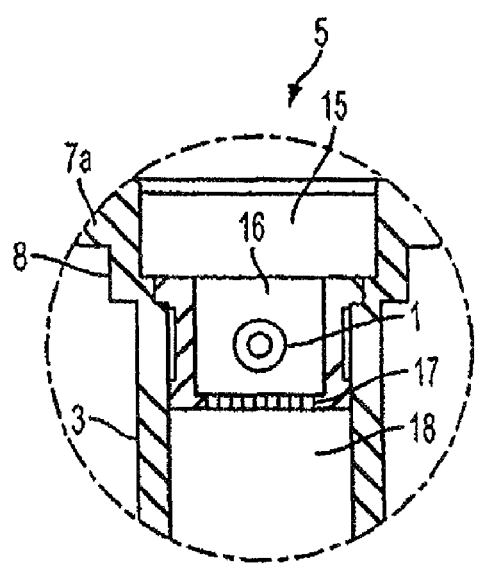

FIG. 1F shows a side view of the inventive column assembly, cut along line C-C of FIG. 1B. FIG. 1G is detail D of FIG. 1E, showing an alternative embodiment for the first top portion 7a. As shown in FIG. 1G, this first top portion 7a slopes downwardly from its top, whereas the first top portion 7 of FIG. 1F is squared off, i.e., non-sloping.

Figure 2A:
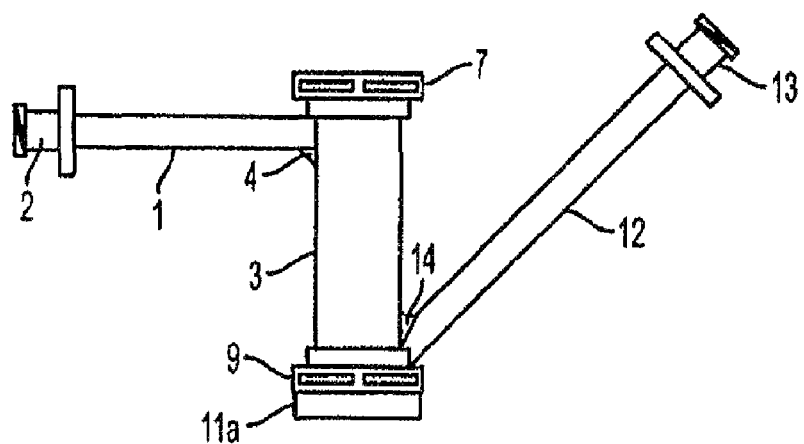
FIGS. 2A-2D show an alternative embodiment of the inventive assembly from different angles and cross sections.
Figure 2B:
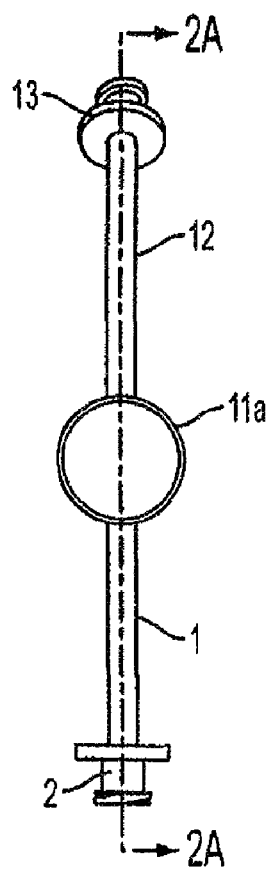
Figure 2C:
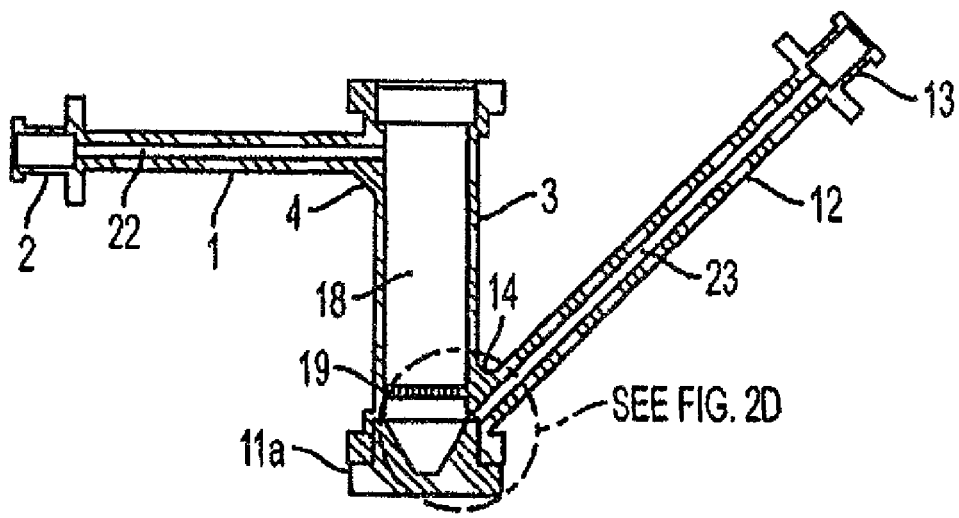
Figure 2D:
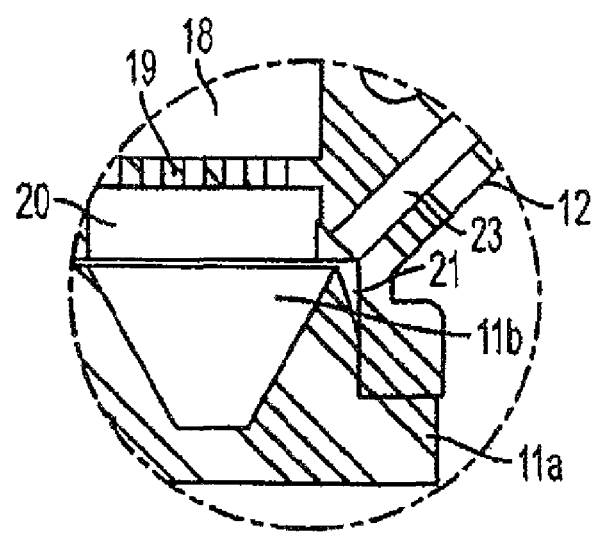

FIGS. 2A-2D show an alternative embodiment of the inventive column assembly. As shown in FIG. 2D, which is detail B from FIG. 2C at a scale of 3:1, the bottom stopper 11a is configured to fit into substantially all of the space of the bottom stopper receptacle area 21. This insures a better fit between the outer wall of the bottom stopper 11a and the inner wall of the bottom stopper receptacle area 21, thus further insuring against any leaks. In addition, the stopper 11a reduces the dead volume in the bottom stopper receptacle area 21. Minimization of the dead volume minimizes mixing with non-radioactive or decayed eluent, which could dilute the fresh eluent, thereby maintaining a narrow rubidium-82 bolus profile. The bottom stopper 11a further comprises a bottom stopper hollow space 11b. This bottom stopper hollow space 11b helps prevent the bottom stopper 11a from blocking the outflow arm 12.

The column assembly is preferably made of polypropylene. Prior art column assemblies were made with H5820 polypropylene. While that product can still be used, in a preferred embodiment the polypropylene random copolymers PP P5M4R-034 or PP 13R9A (Huntsman Polymers (The Woodlands, Tex.)) can be used because they are more resistant to radiation than the prior art H5820 polypropylene. See the Prospector X5 data sheets with ATSM and ISO properties for PP P5M4R-034 and PP 13R9A, which are incorporated herein by reference in their entirety. Of the two Huntsman polypropylenes, PP 13R9A is the more preferred, based upon UV profile, Instron stress testing and appearance after gamma-irradiation.

The manufacturing process for the inventive column assembly has also been improved. A new automatic mold has been designed which increases the quality and appearance of the column assembly, and which increases the efficiency of the manufacturing process. Manufacturing is presently done by Duerr Molding (Union, N.J.).

For example, pins are used to form the hollow portions of the inlet arm 22 and outflow arm 23. In the prior art molding process, these pins were not fixed, so they floated. As a result, the side wall thickness of the inlet arm 1 and outlet arm 12 varied. In the present process, the pins are fixed. Therefore, the thickness of the side walls is more uniform.

Also, as described above, the position of the outflow arm 12 has been moved, the outflow arm no longer protrudes into the hollow interior or lumen of the column 3, and the outflow arm resides in a recess or notch. This prevents the outflow arm from being blocked. Furthermore, support means 4, 14 are provided to strengthen the inlet arm 1 and the outflow arm 12. In addition, notches 24a and 24b are provided for the proper placement of the top basket.

In the inventive column assembly shown in, for example, FIG. 1A and FIG. 2A. The inlet arm 1 and the outlet arm 12 are straight. That is because this is the way the column assembly looks at the end of the molding process. In use, the inlet arm 1 and the outlet arm 12 are curved upward, in much the same configuration as the prior art CardioGen® generator is used.

Further improvement to the manufacturing process and column assembly are described throughout the instant specification.

The packing material area 18 of the column 3 is designed to receive packing material. The type of packing material used depends upon the intended use of the column arrangement.

When used as, for example, a rubidium-82 generator, such as CardioGen®, the packing material is one which will adhere strontium-82 but will allow for the elution of rubidium-82. Strontium(II)-82 decays into rubidium(I)-82. Elution of strontium-82 is not desired because it binds to bone and exposes the patient to unnecessary radiation exposure. Presently, stannic oxide is the preferred packing material.

The packing material is loaded into the column 3 in a conventional manner. The column 3 is then loaded with strontium-82 in a conventional manner. A liquid containing the strontium-82 is slowly added to the top of the packed column and allowed to flow through it by the force of gravity. If necessary, a small vacuum can be used. Also, the packing material is preferably wetted before the strontium-82 is added. Slow addition of the strontium-82 is preferred because it will result in the strontium-82 being absorbed as close to the top of the column as possible.

Filters, preferably fiberglass filters, can also be used in this conventional loading procedure. For example, two fiberglass filters are first placed in the column 3, then a portion of the packing material is added, followed by a single fiberglass filter, then the remainder of the packing material, then two more fiberglass filters. Once filled, the top basket or spacer 17 is inserted into the top basket receptacle area 16. The top basket 17 acts as a retainer to hold the packing material in place.

FIGS. 3A-3D show schematics of the spacer or top basket 26 of the inventive column assembly. The spacer or top basket 26 is cylindrical in shape with an open top portion 27 and a screen 28 at the bottom portion 29. Another top basket or spacer 17 of similar configuration is shown in FIGS. 1A-1G, placed in the top basket receptacle area 16.

Figure 3A:
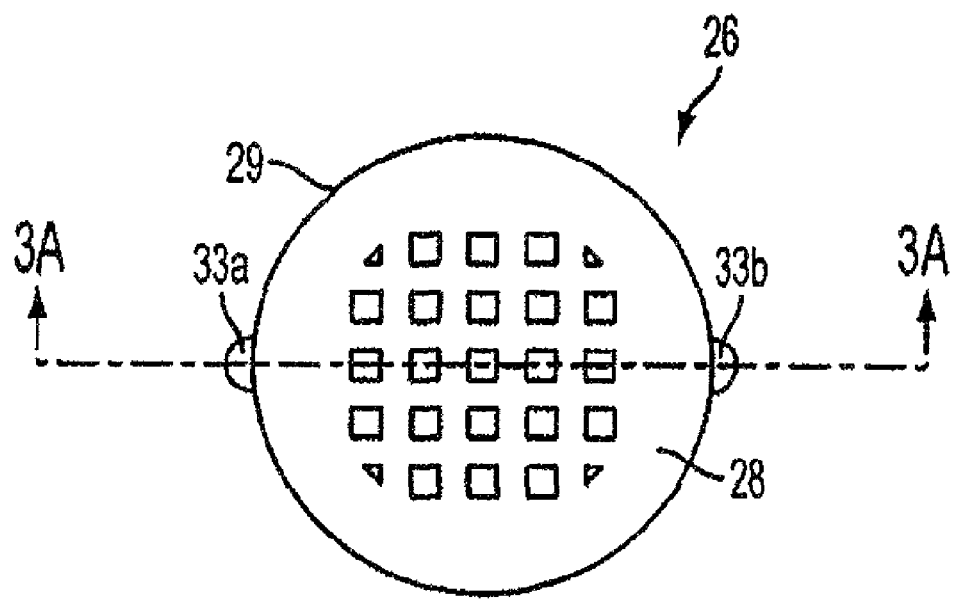
FIGS. 3A-3D show a spacer or basket used in the inventive column assembly.
Figure 3B:
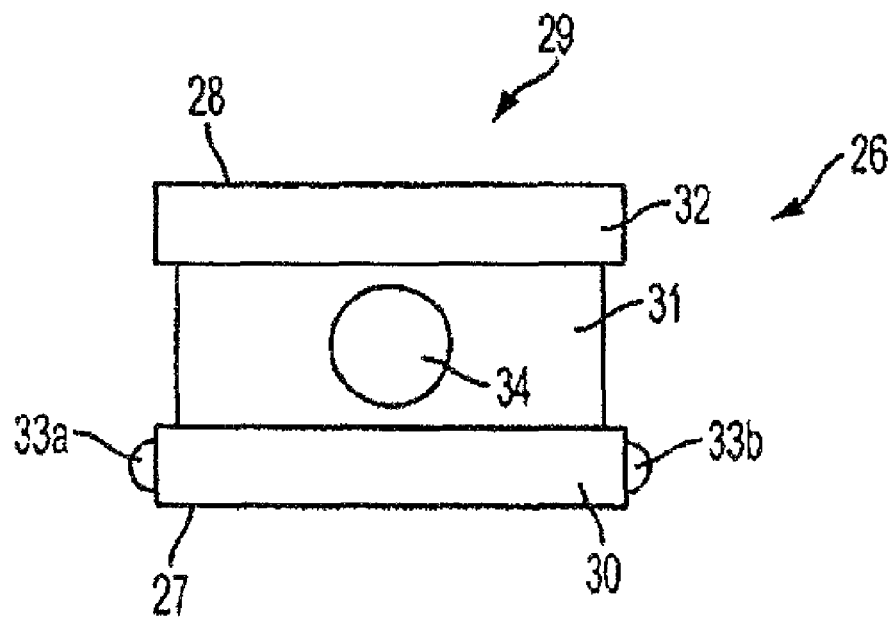
Figure 3C:
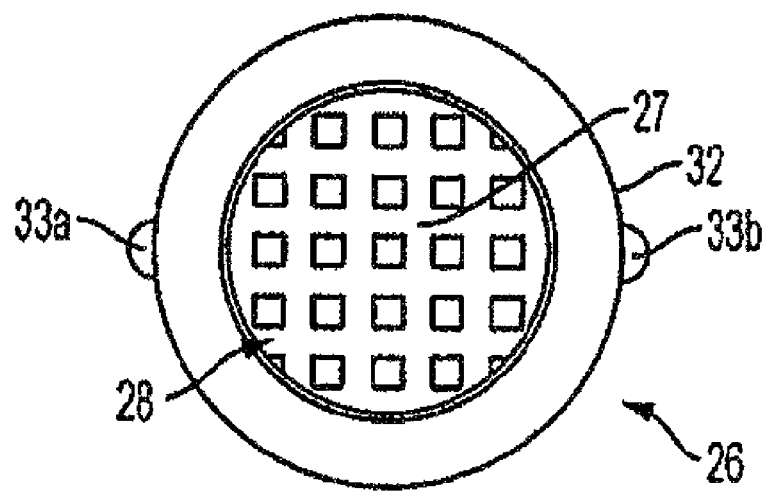
Figure 3D:
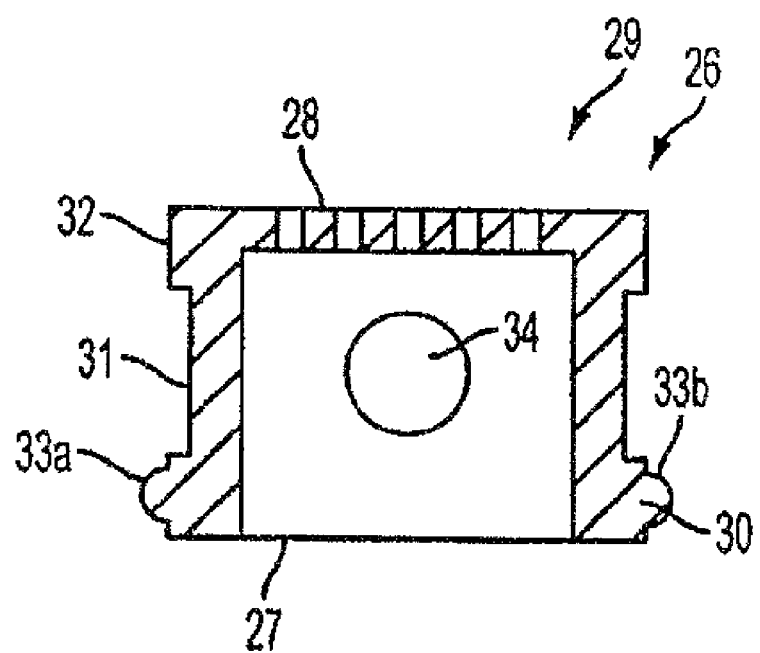

As shown in the embodiment of FIGS. 3B and 3D, the top basket 26 actually has three cylindrical areas, a top cylindrical area 30, a middle cylindrical area 31 and a lower cylindrical area 32. The top 30 and bottom 32 cylindrical areas have diameters about equal to each other, and their diameters are greater than the diameter of the middle cylindrical area 31.

The top basket 26 also contains protrusions 33a, 33b which are designed to cooperate with notches 24a, 24b in the top basket receptacle area 16. In operation, the protrusions 33a, 33b fit into the notches 24a, 24b to insure proper alignment of the top basket 26 in the top basket receptacle area 16. When so positioned, the top basket 26 acts as a retainer to hold the packing material in place.

As shown in FIGS. 3A and 3C, the two protrusions 33a, 33b are 180° opposed to each other. They are located at the top cylindrical area 30. As was the case with the notches 24a, 24b, the present invention is not limited to this configuration. Rather, there can be 1, 3, 4, 5, 6 or more protrusions, in any orientation, so long as they cooperate with the notches to help insure a proper fit for the top basket 26.

The top basket 26 also contains a side opening 34. As shown in FIGS. 3B and 3D, the side opening is in the middle cylindrical area 31 of the top basket 26. The purpose of the side opening is to line up with the inlet arm 1 when the top basket 26 is placed in the top basket receptacle area 16. In this arrangement, when a liquid is introduced into the inlet arm 1, it will pass through the side opening 34 into the top basket 26.

The top basket 26 can be made of any suitable material, such as polypropylene. Preferably, the material will be radiation resistant, i.e. resistant to degradation in the presence of a radioactive material. More preferably, the top basket 26 is made of the same material used to construct the column assembly. In a preferred embodiment, that material is PP P5M4-R-034 or PP 13R9A polypropylene (Huntsman Polymers (The Woodlands, Tex.). Even more preferably, the material is the PP 13R9A polypropylene. In a yet further preferred embodiment, the top basket 26 is molded at the same time the rest of the column assembly is molded.

Figure 4:
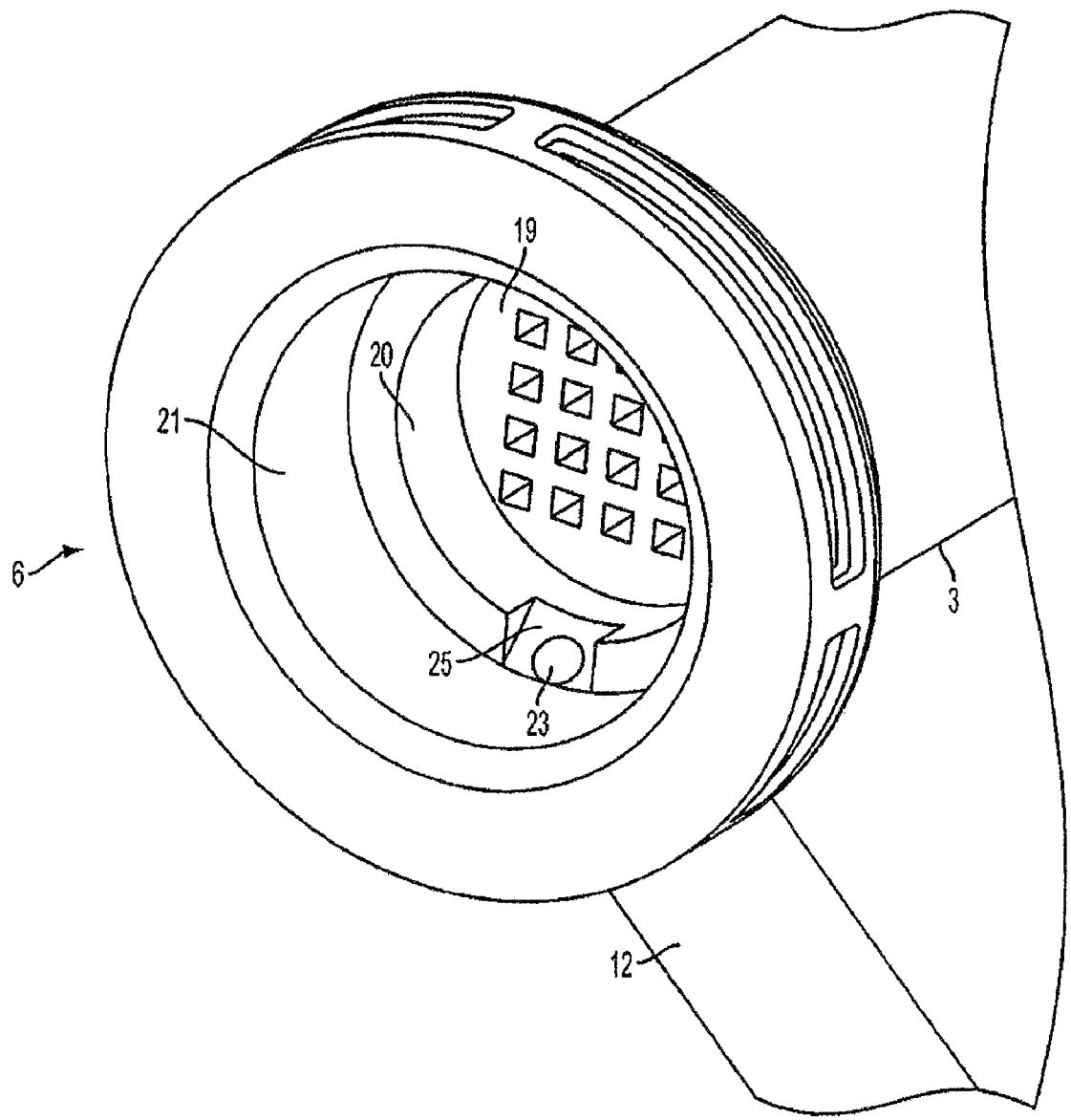
FIG. 4 shows a detailed view of the bottom of the inventive column assembly.

As discussed above, FIG. 4 shows a detailed view of the bottom 6 portion of the column 3. FIG. 4 shows the outflow notch 25 where the hollow portion 23 of the outflow arm 12 intersects the hollow interior of the column 3. The outlet notch 25 prevents blockage of the hollow portion 23 of the outflow arm 12 by the bottom stopper 11 (not shown in FIG. 4).

Figure 5C:
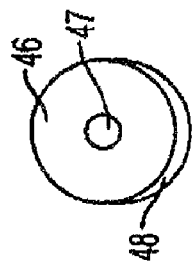
FIGS. 5A-5F show various crimp seals that may be used with the inventive column assembly.
Figure 5F:
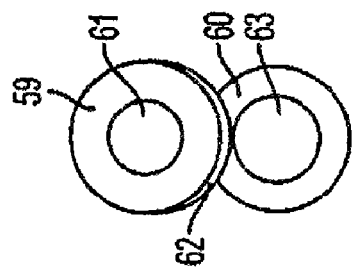

FIGS. 5B-5F show various types of crimp seals to use with the present invention. FIG. 5A shows the current, prior art crimp seal. FIGS. 5B-5F show various alternate embodiments of the crimp seal.

The function of the crimp seal is to form a tight, crimped seal between the stoppers (described below) and the pharmaceutical container to prevent leakage. Also, a central hole is provided in the crimp seal to allow for the insertion of a needle or similar device. In one preferred embodiment the pharmaceutical container is a column, or column assembly, such as one used in a rubidium generator.

The crimp seal can be made of any material, such as plastic or metal. The material should preferably be radiation resistant, and of sufficient strength to withstand pressures of at least 90 psi and preferably up to 160 psi. More preferably, the material should be metal. Preferred metals comprise aluminum, steel and tin, or suitable alloys or mixtures thereof. The metal can be optionally coated. For example, tin coated steel can be used.

The diameter of the crimp seal will vary according to use, for example, vary according to the diameter of the pharmaceutical container which is to be crimped. With respect to a column assembly to be used as a rubidium-82 generator, such as CardioGen®, the diameter of the crimp seal is preferably about 20 mm across its top.

FIG. 5A shows a conventional prior art crimp seal 35. It is made out of aluminum which is about 0.20 mm thick, has a flat top portion 36 with a diameter of about 20 mm with central hole 37 of about 9.5 mm in diameter and a skirt 38 about 7.5 mm high.

There are several potential problems with this prior art crimp seal. First, because aluminum with a thickness of only 0.20 mm is used, the crimp seal might not be strong enough to insure a strong, leakproof seal. Second, the central hole 37 is large, and therefore the stopper might not be properly supported. Also, the larger central hole 37 may allow for ballooning of the stopper. Third, this crimp seal is manually crimped to the column 3. Manual crimping can result in undesirable variability of crimping pressure and, accordingly, can affect how well the crimp seal 35 seals the column 3 to prevent leakage.

Figure 5B:
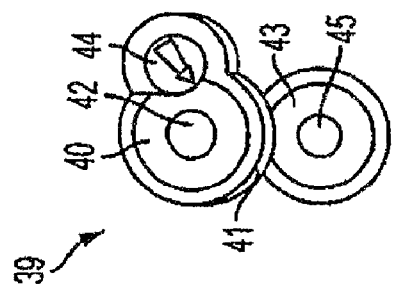

FIG. 5B shows one type of useful crimp seal 39. This crimp seal 39 comprises two parts, a top crimp member 40 and a bottom washer 41. Both the top crimp member 40 and the bottom washer 41 are made of aluminum (vendor—West). The thickness of the aluminum for each part can vary depending upon the intended use, but the aluminum used for each member is generally about 0.20 mm thick.

The top crimp member 40 has a central hole 42 and a skirt 43. The size of each, and the diameter of the crimp seal, can vary depending upon use. As shown in FIG. 5B, the central hole 42 has a diameter of about 6.4 mm and the skirt 43 is about 7.6 mm high. The diameter of the top crimp member 40 is about 20 mm. The top crimp member 40 also has a cover 44, which covers the central hole 42 when not in use but can be pulled or pealed back when in use. Also, while none of FIGS. 5C through 5F or FIGS. 6A and 6B show a cover, it is understood that each of these embodiments can employ a cover if desired.

FIG. 5B also employs a bottom washer 41. The bottom washer 41 contains a central hole 45. The bottom washer central hole 45 can have a diameter greater than, the same as or smaller than the diameter of the central hole 42 in the top crimp member 40. As shown in FIG. 5B, both central holes 45, 42 have about the same diameter, i.e. about 6.4 mm. The bottom washer 41 does not have a skirt. The diameter of the bottom washer 41 is about 20 mm.

When used, the bottom washer 41 is placed below the top crimp member 40 and both are crimped into place. Crimping is preferably performed via an automatic or semi-automatic crimper, which is discussed in more detail below. In the alternative, other processes which control the crimping pressure applied can be used.

FIG. 5C shows another embodiment of the inventive crimp seals. This crimp seal 46 comprises a single member. It is made out of steel (vendor—Microliter). The thickness of the steel can vary according to the intended use, but is generally about 0.20 mm thick. This crimp seal 46 is about 20 mm in diameter, contains a central hole 47 of about 5.0 mm in diameter and has a skirt 48 about 7.2 mm high. The crimp seal 46 is preferably crimped into place using an automatic or semi-automatic crimper, although other processes which control the pressure applied can be used.

Figure 5E:
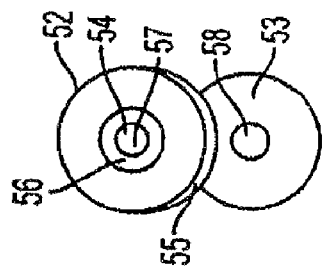
Figure 5A:
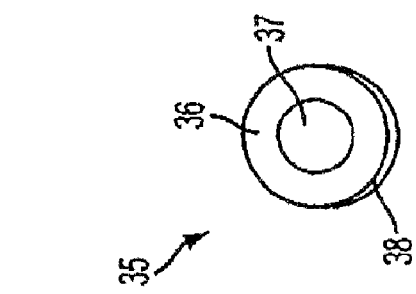
Figure 5D:
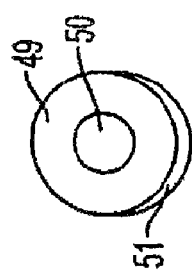

FIG. 5D shows yet another embodiment of the inventive crimp seals. This crimp seal 49 comprises a single member. It is made out of steel (vendor—Microliter). The thickness of the steel can vary according to the intended use, but is generally about 0.20 mm thick. This crimp seal 49 has a diameter of about 20 mm, contains a central hole 50 of about 8.0 mm in diameter and a skirt 51 about 7.2 mm high. The crimp seal 49 is preferably crimped into place using a semi-automatic crimper, although other processes which control the pressure applied can be used.

FIG. 5E is yet still another embodiment of the inventive crimp seals. This embodiment comprises two parts, a top crimp member 52 and a bottom washer 53. Both the top crimp member 52 and the bottom washer 53 are made of aluminum (vendor—Microliter). The thickness of the aluminum can vary depending upon the intended use, but the aluminum used for each member is generally about 0.20 mm thick.

The top crimp member 52 has a central hole 54 and a skirt 55. The central hole 54 has a diameter of about 9.6 mm and the skirt 55 is about 7.6 mm high. The top crimp member 52 has a diameter of about 20 mm.

The top crimp member 52 also contains an insert 56, which is seated in or under the central hole 54. The insert 56 can be made of any suitable substance, but is preferable made of metal, such as steel, aluminum or tin, or plastic. The insert 56 also contains an insert central hole 57, which has a diameter of about 5 mm.

The bottom washer 53 also has a central hole 58, which has a diameter of about 5 mm. The bottom washer 53 is about 20 mm in diameter and it does not have a skirt.

When used, the bottom washer 53 is placed below the top crimp member 52 and the insert 56 and then all are crimped into place. Crimping is preferably performed using an automatic or semi-automatic crimper, although other processes which control the pressure applied can be used.

FIG. 5F shows yet another embodiment of the inventive crimp seals. Like FIG. 5E, FIG. 5F employs two members, a top crimp member 59 and a bottom washer 60. Both members are made of aluminum (vendor-Microliter). While the thickness of the aluminum can vary with the intended use, generally each member is about 0.20 mm thick.

The top crimp member 59 contains a central hole 61 and a skirt 62. The central hole 61 has a diameter of about 9.6 mm and the skirt 62 is about 7.6 mm high. The top crimp member 59 has a diameter of about 20 mm.

The bottom washer 60 also has a central hole 63. The bottom washer central hole 63 has a diameter of about 11.4 mm. The diameter of the entire bottom washer 60 is about 20 mm. The bottom washer 60 does not have a skirt.

When used, the bottom washer 60 is placed below the top crimp member 59. Both are then crimped into place. Preferably, an automatic crimper is employed, although other processes which control the pressure applied can be used.

Figure 6A:
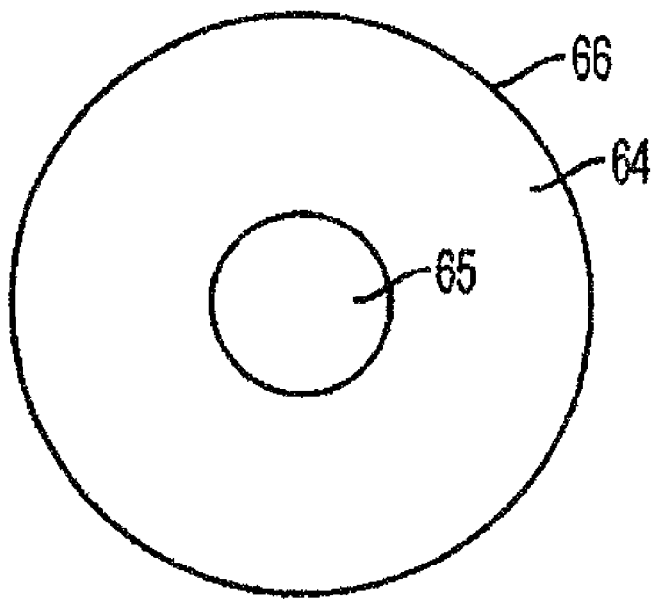
FIGS. 6A and 6B show a preferred crimp seal.
Figure 6B:
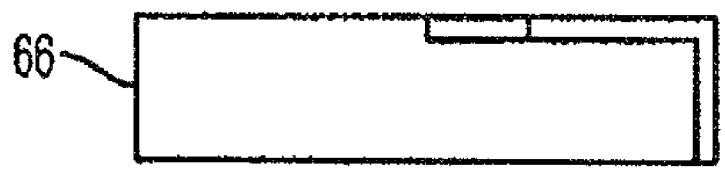

FIGS. 6A and 6B show an alternate and preferred embodiment of the inventive crimp seals. This crimp seal 64 comprises a single member. It is made out of steel (vendor—Microliter), code #20-000 M. See the Microliter Product Catalog, which is incorporated herein by reference in its entirety. The thickness of the steel is about 0.20 mm.

The crimp seal 64 contains a central hole 65 and a skirt 66. The central hole 65 is about 5.00 mm±0.25 mm in diameter and the skirt 66 is about 7.00 mm±0.25 mm high. The entire crimp seal 64 has a diameter of about 20.75 mm±0.25 mm. The crimp seal 64 is preferably crimped into place using an automatic or semi-automatic crimper.

FIGS. 7A-7D show an improved stopper 67 to be used with the inventive column assembly. The stopper 67 is preferably made from a material which will form a tight seal with the column assembly. In a preferred embodiment the stopper 67 is made of a material which is also resistant to radiation.

Prior art stoppers were made of materials such as Itran-Tompkins PT-29 green neoprene rubber. This material had two potential disadvantages. First, it could degrade when exposed to radiation. Second, it contained latex, which could cause allergic reactions.

Various materials were compared to the PT-29 green neoprene used in the prior art. These materials included neoprene, isoprene, bromobutyl, chlorobutyl, nitrile, isoprene/chlorobutyl, EPDM (ethylene propylene diene monomer) and Viton. These materials were coated, uncoated, siliconized and non-siliconized.

These materials were made into column assembly stoppers and were irradiated simulating the exposure from a 100 mCi generator over a time period of 45 days (about 145 kGy). Irradiated stoppers were compared to non-irradiated controls by integrity (pressure) testing of the column/stopper assemblies. Assemblies were pressurized to determine load pressure required to cause ballooning of rubber materials or leaks/burst at the seal closure (up to about 200 psi). In addition, for the purpose of determining potential rubber extractables and/or leechables, additional column/stopper assemblies were irradiated in the presence of 0.9% saline solution. The saline solution was then scanned at 250 mm for UV absorbing extractables.

Three compositions were identified as suitable to use in stoppers: West Pharmaceutical Services (Lionville, Pa.) 4588/40 isoprene/chlorobutyl; American Stelmi (Princeton, N.J.) 6720 bromobutyl; and Helvoet-Pharma (Pennsauken, N.J.) Helvoet FM 140/0 chlorobutyl. Of these materials, the most preferred product to use is the West 4588/40 isoprene/chlorobutyl.

The stopper 67 should be configured so that it forms a tight seal with the column assembly and minimizes the dead volume (mixing), thus maintaining a narrow rubidium-82 bolus profile and maximizing efficiency. One preferred structure for the stopper is shown in FIGS. 7A-7D.

Figure 7A:
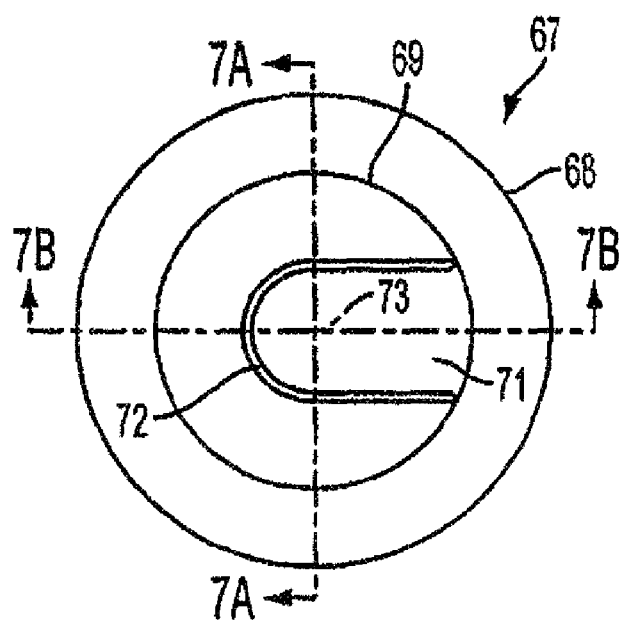
FIGS. 7A-7D show a stopper for use with the inventive column assembly.
Figure 7B:
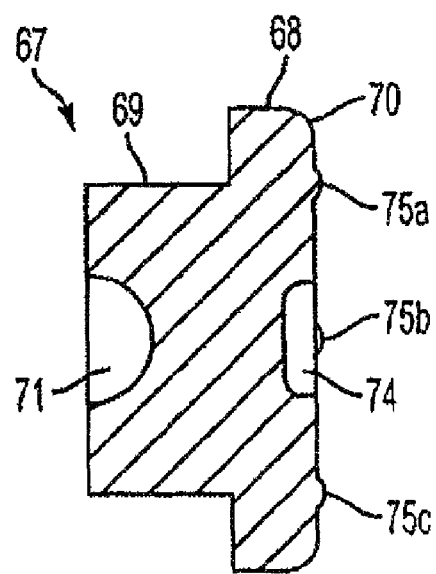
Figure 7C:
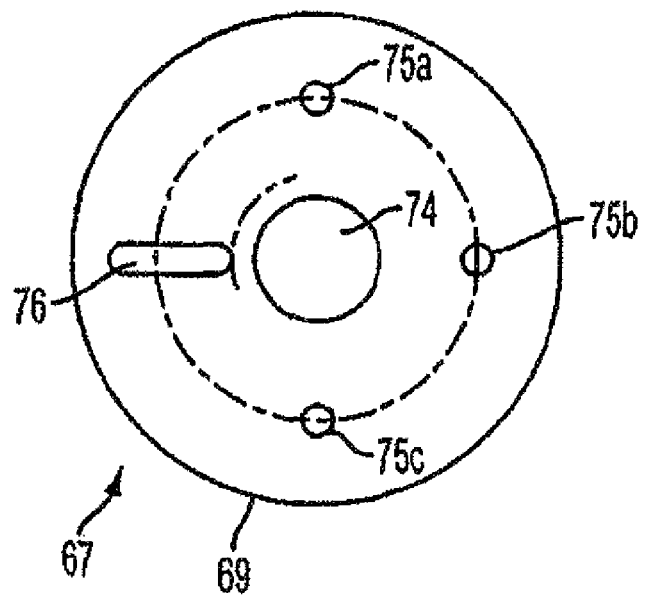

Referring to FIG. 7B, the stopper 67 comprises a generally cylindrical top section 68 and a generally cylindrical bottom section 69. The diameter of the stopper bottom section 69 is about the same as or slightly larger than the inside diameter of the first top portion 7 and first bottom portion 9 of the cylinder 3, assuming both of these portions 7, 9 have the same diameter. If these portions have different diameters, then the cylindrical bottom section 69 of the stopper 67 will have about the same or slightly larger inside diameter as the portion 7, 9 it is intended to be inserted into. The reason for this configuration is to insure a tight fit between the stopper 67 and the first top 7 and first bottom 9 portions of the cylinder 3. A tight cylinder 3/stopper 67 interface helps prevent leakage.

The stopper top section 68 has a greater diameter than the stopper bottom section 69 to prevent the stopper 67 from being inserted too far into the cylinder 3. In addition, optionally the stopper top section 68 can have a curved upper edge 70.

The stopper bottom section 69, in one preferred embodiment, contains a U-shaped groove 71 in its base. See FIG. 7A. The U-shaped groove 71 traverses greater than half the length of the stopper bottom section 69, and it terminates in a semicircular section 72. Preferably, the center point 73 of the semicircular section 72 should be about at the center point of the stopper bottom section 69.

Figure 7D:
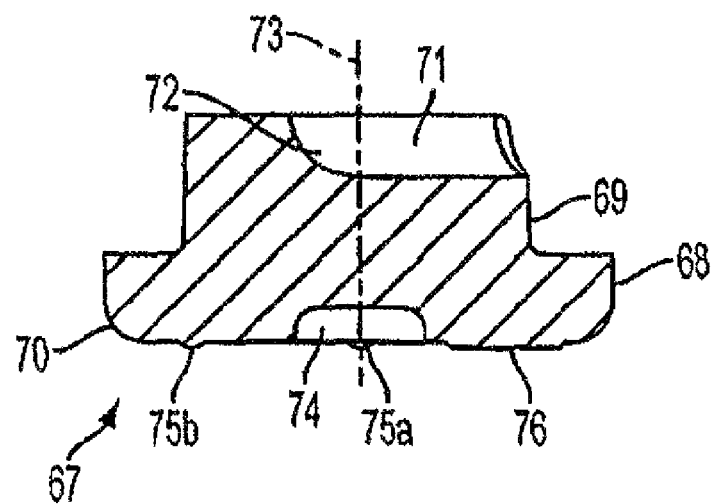

The stopper top section 68 contains a central circular indentation 74 in its top surface. See FIG. 7C. Preferably, the diameter of the central circular indentation 74 has a diameter about equal to the width of the U-shape groove 71. As shown in FIGS. 7B and 7D, the central circular indentation 74 and the U-shaped groove 71 should preferably line up with each other when the stopper is viewed through its cross-section. The central circular indentation 74 and U-shaped groove 71 allow for easy insertion of a needle or similar device into the stopper 67.

The surface of the stopper top section 68 also contains three spherical dots 75a, 75b, 75c and an indicia, such as a spherical lug 76. They are spaced equidistant from each other around the central circular indentation 74. Also, the spherical lug 76 is placed so that it is above the U-shaped grove 71. In this configuration, when the stopper 67 is inserted into the first top portion 7 of the column 3, the spherical lug 76 can be lined up with the inlet arm 1. Thus, the open end of the U-shaped groove 71 will face the inlet arm 1, thus preventing its blockage.

The same holds true for the first bottom portion 9 of the column 3. When the stopper 67 (stopper 11 shown in FIGS. 1A-1G and stopper 11b in FIGS. 2A-2D can have the same or different configurations from stopper 67) is inserted therein, the spherical lug 76 is lined up with the outlet arm 12. The open end of the U-shaped groove 71 will then face the outlet arm 12 and prevent its blockage.

It is understood that the present invention is not limited to a U-shaped groove 71. Any other configuration, such as a notch, can be used so long as any potential blockage is avoided. In fact, if there is no potential for blockage, the U-shaped groove 71 or alternative structure can be eliminated.

The stopper 67 is affixed to the column 3 via crimping, using the crimping seals described above in FIGS. 5 and 6. In the prior art, crimping was performed manually. The disadvantage of manual crimping is that it is not always uniform. One problem this can cause is leakage. To overcome this potential problem, the present invention preferably uses automatic or semi-automatic crimping.

Any automatic or semi-automatic crimper can be used for the present invention, so long as it can consistently crimp seals at a specified, controlled pressure. One preferred type of automatic crimper is a pneumatic crimper, which is powered by gas. One example of a pneumatic crimper suitable for the present invention as an AP/CP2000 Lightweight Air Crimper/Decapper (Laboratory Precision Limited, UK). See Laboratory Precision Limited brochure copyrighted Apr. 4, 2001, which is incorporated herein by reference in its entirety.

In the crimping process, a stopper 67 is inserted into the top portion 5 or bottom portion 6 of the column 3, so that it is seated in the first top portion 7 or first bottom portion 9, respectively. A crimp seal or a crimp seal and washer (see FIGS. 5 and 6) is/are placed over the stopper 67. The crimp seal or crimp seal and washer are then crimped into place, either manually or, preferably, automatically or semi-automatically. While the crimping pressure used is optimized based upon the configuration and material of the crimp seal and stopper, generally about 117±3 psi pressure is used.

The resulting crimped crimp seal/stopper configuration can withstand the operative pressures of the system, i.e. at least 90 psi and preferably up to 200 psi.

When in operation, connector tubes (not shown) are connected to the column assembly. Referring to FIG. 1A, both the inlet arm 1 and the outlet arm 12 have a female Luer cap 2, 13 at their distal ends. These female Luer caps 2, 13 engage male Luer caps at the proximal ends of the connector tubes.

Prior art connector tubes can discolor from clear to brown and harden upon prolonged exposure to radiation. Also, the Luer connector can discolor and become brittle. In addition, the Luer connectors can loosen or become unintentionally disconnected during use.

Accordingly, the present invention includes constructing connector tubing out of radiation resistant materials. Preferably, the tubing is made from a flexible radiation resistant polyvinyl chloride (PVC) and the Luer connector is made from a rigid radiation resistant PVC. For example, a preferred material for constructing the tubing is AlphaGary PVC 2232 A/R-78S Clear 030X. See AlphaGary Test Result Certificate, Report Date Aug. 20, 1999; Technical Data, Date of Origin 8/99; and Material Safety Data Sheet printed Apr. 5, 2000; which are incorporated herein by reference in their entirety. A preferred material for constructing the Luer connector is AlphaGary PVC 2212 RHT/1-118 Clear 080X. See AlphaGary Data Sheet, Revision Date 4/02, which is incorporated herein by reference in its entirety. Also, using this AlphaGary rigid PVC for the Luer connector allows the heat bonding of tubing to the Luer connector.

In an alternative embodiment of the present invention, the distal end of the connector tube attached to the outlet arm 12 of the column assembly as shown in FIG. 1A has a check valve (not shown) attached to it. In a preferred embodiment, the check valve is included in the patient tube 103, shown in FIG. 9, either before or after the patient sterilization filter 104. The check valve prevents a back flow of fluids from entering the connector tube when connected to or disconnected from a patient.

In another alternative embodiment, sometimes the generator is placed so far away from a patient that the patient tube cannot reach all the way to the patient. In this instance, one or more extension tubes can be added, the length of which is sufficient to reach the patient. Preferably, a single extension tube is used and in a preferred embodiment, it is made of the same materials as the connector tubes discussed above to provide for, e.g., flexibility and radiation resistance.

The present invention further includes an improved Luer lock. The improvements are described below. An embodiment of this improved Luer lock is set forth in FIGS. 8A-8D. These improved Luer locks can be used with the pharmaceutical containers of the present invention, or in any other indication where it is desirable to have a connection that will not loosen or inadvertently disconnect.

In the embodiment of FIGS. 8A-8D, FIG. 8A show a side view of the inventive column assembly with the inlet arm 1 projecting forward. Also shown is the female Luer cap 2 at the distal end of the inlet arm 1.

Figure 8A:
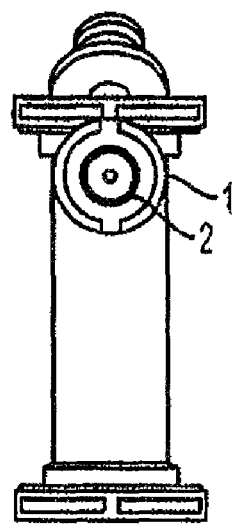
FIGS. 8A-8D show an improved Luer lock.
Figure 8B:
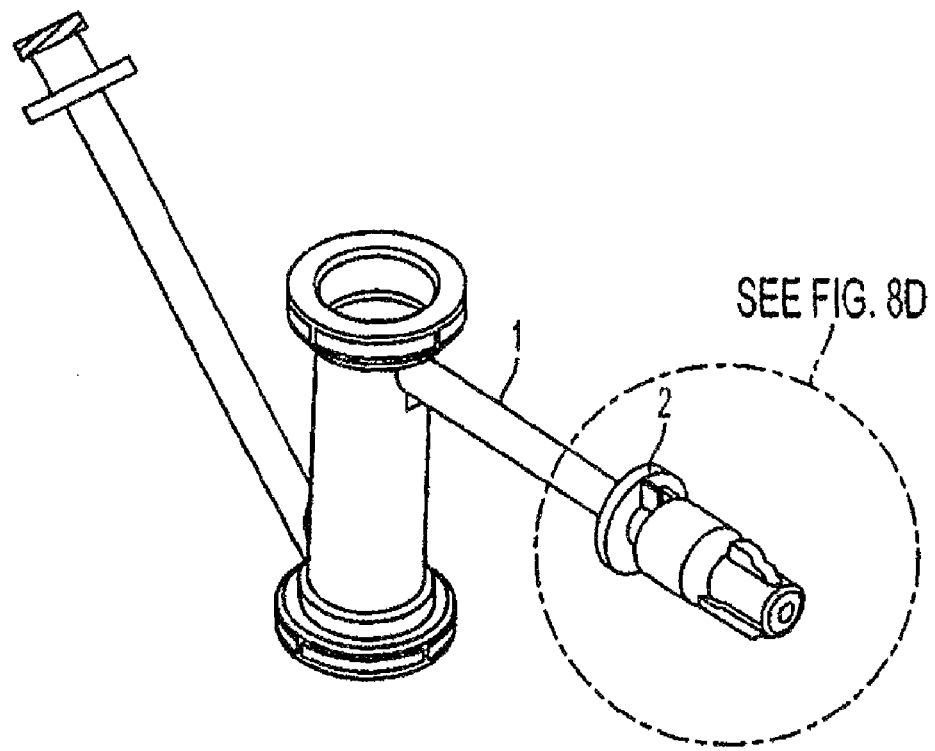
Figure 8C:
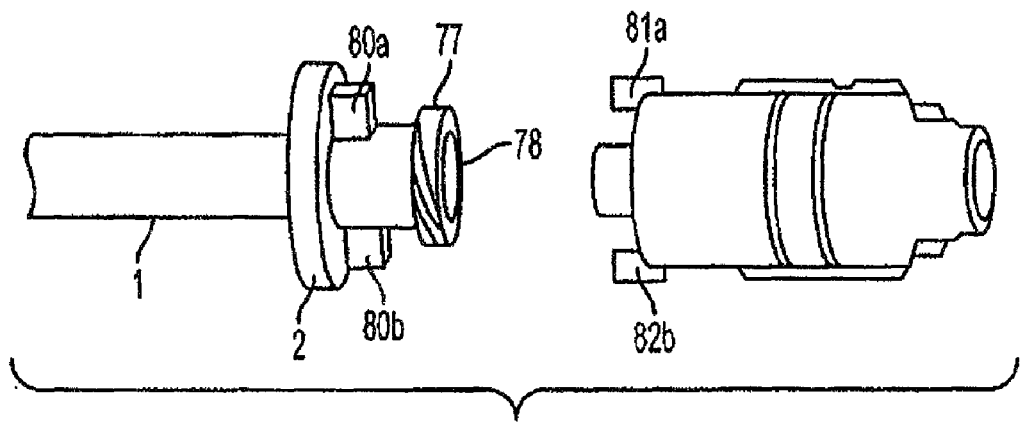

As shown in FIG. 8C, the female Luer cap 2 terminates in a flange 77. The flange 77 can be flat or, as shown, contain a groove 78. Other configurations, known in the art, can also be used.

Figure 8D:
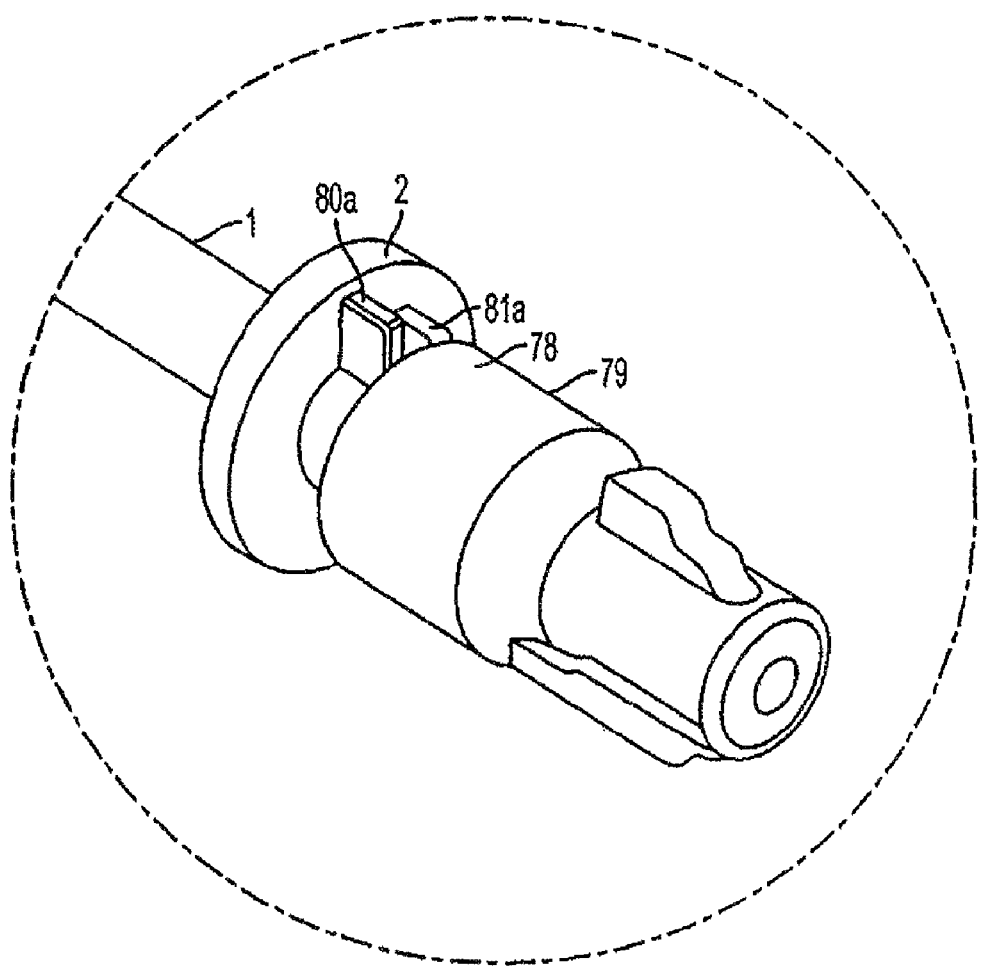

The flange 77 is configured to engage and mate with threads 78 in a male Luer cap 79. When the two caps 2, 79 are screwed together, they form a tight Luer lock which will be leak resistant. This configuration is shown in FIG. 8D.

One difficulty with a Luer lock is to know when the male and female caps 79, 2 have been connected sufficiently to form a tight lock. To overcome this problem, one or more tabs are provided on each of the male 79 and female Luer caps 2. As shown for example in FIGS. 8C and 8D, two tabs are provided on each cap 80a, 80b, 81a and 81b, although it is understood that the invention is not limited to this configuration only. For example, each of the Luer caps can also contain 1, 3, 4, 5, 6 or more tabs.

In one embodiment, the female Luer cap tabs 80a, 80b and the male Luer cap tabs 81a, 81b are so positioned that when the Luer locks is sufficiently tight, the tabs line up with each other. This way, a user knows when tightening is completed. The present invention, however, is not limited to this one configuration, so long as the tab or tabs on each of the Luer connectors 79, 2 are arranged in a desired configuration to demonstrate that the Luer connectors 79, 2 are sufficiently tightened. In another preferred embodiment, as shown in FIG. 8D, the male Luer cap tabs 81a, 81b overlap with the female Luer cap tabs 80a, 80b. The tabs are so positioned that this overlap occurs when the tightening is complete. At the point of desired tightening, the tabs 80a, 80b, 81a, 81b pass by or click past each other. That way, the Luer locks cannot be over- or under-tightened. Also, loosening or disconnection of the Luer lock during use is prevented by the overlapping of the tabs, preventing the Luer connectors 79, 2 from turning in a loosening direction.

Although the inventive Luer locks are shown only as part of the generator as shown in FIGS. 8A and 8B, the inventive Luer locks can be used in place of conventional Luer locks at any place in the inventive generator system. Moreover, the inventive generator system can contain a combination of conventional Luer locks and the inventive Luer locks. Finally, the inventive Luer locks are not solely intended for use with the inventive generator system. Rather, they can be used in place of conventional Luer locks wherever those conventional Luer locks are used.

When the inventive column assembly is used as, for example, a rubidium-82 generator, it is pre-packaged with strontium-82 in the factory. That is, the product shipped to the customer is radioactive. Therefore, the radioactive column assembly is shipped in a shielded (e.g. lead) container.

Nevertheless, leakage is still a concern upon shipping. Thus, to improve safety when the radioactive column assembly is shipped, an inventive improvement is to ship the product with a liquid absorbent pad. Preferably, the shipping pad is a GP100 absorbent pad (Shell Packaging Corporation, Springfield, N.J.). GP100 is a 100% polypropylene non-woven mat of randomly oriented micro-fibers (2-10 micron diameters). See SPC General Product Specifications for GP100 dated May 26, 2003, which is incorporated herein by reference in its entirety. This type of shipping pad is useful in absorbing any leaks which may occur.

SUMMARY OF THE PREFERRED EMBODIMENTS

Improved Seal

The new seal, which is used to crimp the rubber stopper in place in a pharmaceutical container and particularly, which is used to seal a radioisotope generator column/stopper assembly system, such as CardioGen®, is preferably made of a sufficiently strong material to eliminate the problems discussed above. FIGS. 5B through 5F and FIGS. 6A and 6B illustrate various method of reinforcing the top portion of the seal by use of a second layer (washer) or use of a stronger material such as steel/tin in addition to reducing the size of the center hole. The material may include metal or plastic, but is preferably metal. The metal may include heavy gauge aluminum, steel or tin, but is preferably steel or tin. The seal generally has the configuration shown in FIGS. 5B through 5F and FIGS. 6A and 6B and may have a small or large central hole, a shorter or longer skirt and optionally, a cover (e.g., plastic or aluminum over the central hole). The dimensions of the seal will vary, and one skilled in the art will understand that they should be appropriate to the container which is being sealed. Approximate dimensions for seals for a radioisotope generator column are shown in the various examples in FIGS. 5B through 5F and in FIGS. 6A and 6B. These dimensions are approximate and are not intended to be limiting.

The central hole of the seals of the invention may vary in size. In a preferred embodiment the seal has a smaller central hole such as, for example, those proportional to the central holes shown in FIG. 5B, FIG. 5C, FIG. 5E and FIGS. 6A and 6B.

In one embodiment, seals of FIG. 5B through FIG. 5F and FIGS. 6A and 6B are used to seal a radioisotope generator column. These seals are available from the vendors West Pharmaceutical Services (Lionville, Pa.) and Microliter Analytical Supplies Inc. (Suwannee, Ga.). In a particularly preferred embodiment, the central hole of the seal is reduced in size such as in the seals in FIG. 5B, FIG. 5C, FIG. 5E and FIGS. 6A and 6B. The preferred configuration for this application is a 1-piece steel/tin crimp with a center hole of approximately 4-5 mm diameter and a skirt length of approximately 7.2 to 7.5 mm as shown in FIGS. 6A and 6B.

The combination of using a stronger material such as steel/tin or heavier gauge aluminum and reduction of the center hole results in optimum performance in maintaining a secure leakage free seal under high pressure and particularly repeated exposure (pulsing or cycling) to high pressure as occurs with the use of the rubidium-82 generator as the enlarged surface area of the crimp limits excessive expansion of the rubber closure under pressure.

The use of a stronger material such as steel/tin or heavy gauge aluminum further improves the performance of the crimp by reducing the likelihood of failure due to relaxation or fatigue of the seal flange which is formed at the point where the crimp skirt is folded under the column or container flange when exposed to high or pulsating pressures. It is understood that the skirt length can be varied to provide a proper fit with the container/rubber seal combination to which it is applied.

Automatic Crimper and Improved Crimping Process

In a preferred embodiment, an automatic or semi-automatic crimper is used to crimp the seals of the invention. The automatic or semi-automatic crimper is set at an optimized pressure and is able to crimp seals of any material during assembly of a pharmaceutical container such as a radioisotope generator column/stopper assembly system. Suitable automatic crimpers include pressurized and/or compressed air crimpers such as those available from Laboratory Precision Limited under the trade name/model number AP/CP2000. Use of the automatic or semi-automatic crimping procedure of the invention with compressed or pressurized air results in consistent/reproducible crimping pressures, and enables selection of optimized crimping pressures when crimping various seal materials.

Use of optimized pressures improves the performance of the seals of the invention and also improves performance of seals of only moderate strength, such as lighter gauge aluminum and some plastics.

The automatic or semi-automatic, pneumatically powered crimper used to apply the seal is preferably operated at an optimized pressure of between 60-140 psi. However, although automatic or semi-automatic crimpers are preferred, it should be noted that application of the seal is not limited to automated equipment, and systems ranging from manual to fully automatic may be used, provided their operation can be optimized to produce repeatable and consistent predetermined pressures in applying the seals.

Column Design Improvements

Manufacturing Process To create the new column design, a new automatic mold has been designed. The mold and the new columns produced therein exhibit improved column quality and appearance. The new mold also increases the efficiency of the manufacturing process. The increased speed of the new automated mold enables one operator to run the process efficiently.

Column Design The improved pharmaceutical container also includes improvements to the design which ensure specified flow of eluent through the container and improve its packing and consistency. In one embodiment the improved container comprises a column used in a radioisotope generator. The improved column includes a repositioned outlet arm, and the column outlet resides in a recess or notch in the inside ledge of the column where the outlet arm enters the column lumen, to prevent a stopper from blocking the flow. These improvements further include introducing small reinforcement pieces of resin to the outside of the column between the outlet arm and column body and between the inlet arm and column body to provide additional strength. Additionally, the seam of the inlet and outlet arms has been eliminated by changing the mold runners. This change has improved the consistency of the inlet and outlet arm diameters and made the arms stronger.

Furthermore, to address consistency of packing of the containers, two small alignment slots have been cut into the wall of the column to receive the orientation knobs on the baskets that properly align and seat the basket in the column and limit the insertion depth into the column. This improves the consistency of packing density and eliminates potential blockage of the inlet arm. Additionally, in one embodiment, the improved column has stopper flanges and Luer flanges with much smoother surfaces with sharper edges to improve the sealing ability of the crimp. These attributes improve stopper and Luer contact to the column and greatly reduce the chance of leakage. Also, the flashing on the column is reduced greatly to enhance the appearance of the part.

Finally, the column assembly is made from a radiation resistant or tolerant material. The most preferred material is Huntsman PP 13R9A polypropylene.

Luer Lock and Connector Tube Improvements

The Luer locks and connector tubes used with the column have also been improved. First, the connector tubes are made from a radiation resistant or tolerant material. Preferably, this material is AlphaGary PVC 2232 A/R-78S clear 030X.

Second, the terminal end of the connector tube which attaches to the column contains a male Luer cap. This male Luer cap is made of a radiation resistant material, preferably AlphaGary PVC 2212RHT/1-118 clear 080X.

Third, the male and female Luer caps screw together and each contains tabs, preferably two tabs each. When the tabs line up with each other in one embodiment or overlap with each other in another embodiment, that indicates that the two Luer caps are sufficiently tightened or screwed together to form a tight seal or lock. Also, in a preferred embodiment the overlapping tabs prevent the Luer caps from becoming loose, i.e. unscrewing.

Figure 9:
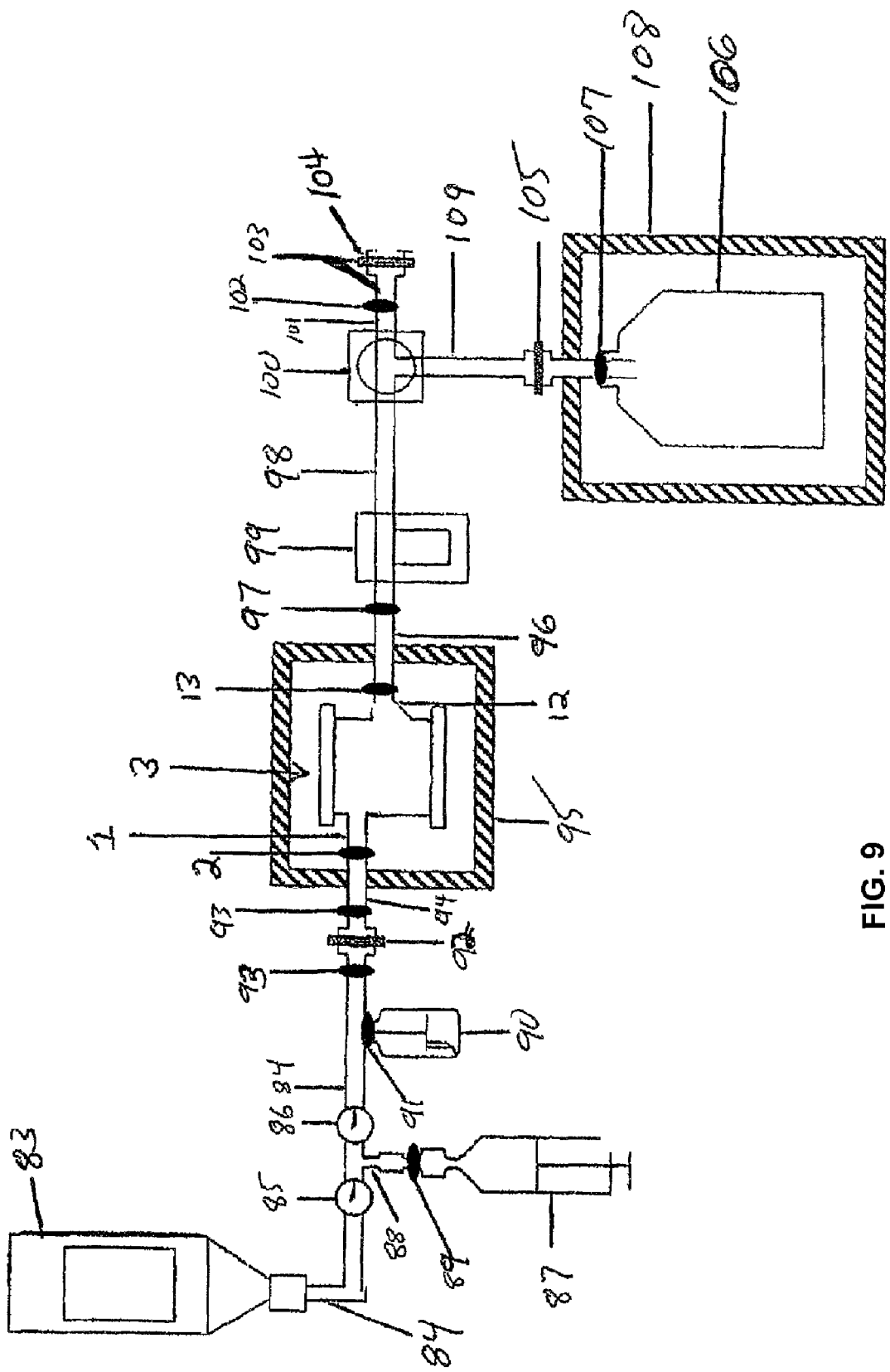
FIG. 9 is a diagram of the entire radionucleotide generator system.

FIG. 9 is a diagram of the entire radionucleotide generator system. In this system, a saline supply 83 is connected to a saline supply tube 84. The saline tube 84 passes through a first check valve 85 and a second check valve 86. The check valves 85, 86 are used to insure that the saline solution only flows in the direction of the rubidium generator column 3. Interspersed between the check valves 85, 86 is a syringe pump 87. The syringe pump 87 connects to saline supply tube 84 at a T-junction 88 via a syringe pump luer connection 89.

After the second check valve 86, a pressure transducer 90 is connected to the saline supply tube 84 via a pressure transducer luer connection 91. The saline supply tube 84 terminates at a first sterilization filter 92 and is connected to it via a first sterilization filter luer connection 93.

The sterilization filter 92 is connected to a column connector tube 94 via a column connection tube luer connector 93. The column connector tube 94 passes through a generator shield 95 and connects to the female luer cap 2 of the inlet arm 1 via a male luer cap as shown in FIG. 8D. The generator shield 95 prevents exposure to radiation from the column 3 which can contain radioactive materials, such as strontium and rubidium-82. The inlet arm 1 is connected to the column 3 which is connected to the outlet arm 12 as shown in, for example, FIGS. 1 and 2. The female luer cap 13 of the outflow arm 12 connects to the male luer cap (not shown) of outlet connecting tube 96.

The outflow connecting tube 96 passes through the generator shield 95 and connects via an outflow connecting tube luer connector 97 to a divergence valve tube 98. The divergence valve tube 98 passes through a positron (beta) detector 99, which is used to insure that the liquid to be injected into a patient has the correct level of radioactivity. Recall that at this point the liquid, which is usually a saline solution and starts at the saline supply 83, has now passed through the column 3 and thus, will contain rubidium-82.

After the positron (beta) detector 99, the divergence valve tube 98 passes to a divergence valve 100. The divergence valve 100 will divert the liquid to either the diversion outlet tubing 101 or a waste connection tube 102. The diversion outlet tubing 101 connects via the patient tube-luer connection 102 to a patient tube 103, which terminates at a patient sterilization filter 104 which is solvent bonded at the time of manufacture to the patient tube 103. A needle may be attached to the patient sterilization filter 104.

The patient tube 103 can pass directly to a patient (via the patient sterilization filter 104). In an alternative embodiment, the patient tube 103 can include a check valve prior to the patient sterilization filter 104. The check valve may be solvent bonded at the time of manufacture of the assembly (not shown). The check valve can be connected to the patient tube 103 by a check valve luer connection (not shown) which may be solvent bonded at the time of manufacture of the patient line. In yet another alternative embodiment, the check valve can be connected after the patient sterilization filter 104, optionally via a luer connection. Also, as described above, if the distance to the patient is too great, one or more additional connector tubes (also called extension tubes) (not shown) can be added to the assembly to bridge the distance to the patient. For example, one or more extension tubes may be connected with a luer fitting between the patient tube luer connection 102 and the patient tubing 103.

The waste connector tube 109 passes through a waste sterilization filter 105 to a waste bottle 106, and these can be connected to each other via a waste luer connection 107. The waste bottle 106 is surrounded by a waste shield 108 to prevent exposure to radiation.

The system shown in FIG. 9 and discussed above contains a number of luer connections. Some or all of these luer connections can be the inventive luer connections described above. Conversely, some or all of the luer connections can be of the conventional type, or do not even have to be luer connections at all, but rather can be any type of connectors, and can be jointly referred to as "connecting means". Preferably, some or all of the connecting means are of the inventive type while the remainder are conventional luer connections.

In addition, the tubes and connecting means are preferably made of radiation resistant materials. Preferably, they are made of the materials discussed above. This is especially true of those tubes and connecting means which are exposed to radiation.

Shipping Improvements

The columns can be shipped pre-loaded with, for example, strontium-82. Therefore, the columns are shipped in sealed containers containing GP-100 absorbent material to absorb any leakage.

The above description is to be taken as illustrative and not in the limiting sense. Many modifications can be made to the design without deviating from the scope thereof.

What is claimed is:
1. An improved rubidium-82 generator comprising:
    a. a hollow column with a top portion, a middle portion and a bottom portion, said top portion including one or more notches, and a screen separating the middle portion and the bottom portion;
    b. a top basket with one or more protrusions, said one or more protrusions configured to cooperate with the one or more notches in the top portion of the hollow column so as to cause the proper seating of the top basket in the top portion of the hollow column, said top basket further comprising a screen at its base and a side opening;
    c. an inlet arm which intersects the hollow column at its top portion at a point where the inlet arm is aligned with the side opening in the top basket, and further wherein the inlet arm has a female Luer cap at its distal end, said female Luer cap containing one or more tabs on its outer surface;
    d. an outlet arm which intersects but does not protrude into the hollow column at its bottom portion, wherein a notch is provided at the point of intersection on the bottom portion's inner surface, and further wherein the outlet arm has a female Luer cap at its distal end, said female Luer cap containing one or more tabs on its outer surface;
    e. support means to support the inlet arm and the outlet arm to the hollow column;
wherein said hollow column, top basket, inlet arm, outlet arm and support means are constructed of a radiation resistant polypropylene;
    f. a packing material comprising stannic oxide with strontium-82 adhered thereto, said packing material placed in the middle portion of the hollow column above the bottom screen and below the screen of the top basket;

g. a top stopper comprising a radiation resistant material, said top stopper configured to form a tight seal with the top portion of the hollow column but which does not block the inlet arm;

h. a bottom stopper comprising a radiation resistant material, said bottom stopper configured to form a tight seal with the bottom portion of the hollow column and minimizing a dead space in the bottom portion of the hollow column, without blocking the outlet arm;

i. a first crimp seal to crimp the top stopper to the top portion of the hollow column and a second crimp seal to crimp the bottom stopper to the bottom portion of the hollow column, wherein each crimp seal comprises steel with a thickness of about 0.2 mm and a central hole about 5.0 mm in diameter, wherein each crimp seal is crimped to a pressure of about 117 psi;

j. a first flexible tube comprising a flexible, radiation resistant polyvinyl chloride with a first male Luer cap comprising a rigid, radiation resistant polyvinyl chloride at one end of said first flexible tube, said first male Luer cap being configured to cooperate with the female Luer cap at the distal end of the inlet arm, so that the first male Luer cap and the female Luer cap at the distal end of the inlet arm can be screwed together to form a tight Luer lock, and wherein said first male Luer cap contains one or more tabs on its outer surface which will align with the one or more tabs on the outer surface of the female Luer cap at the distal end of the inlet arm, when the two Luer caps are screwed together, so as to achieve a desired configuration, with respect to each other, when the Luer caps are tightened together; and k. a second flexible tube comprising a flexible, radiation resistant polyvinyl chloride with a second male Luer cap comprising a rigid, radiation resistant polyvinyl chloride at one end of said second flexible tube, said second male Luer cap being configured to cooperate with the female Luer cap at the distal end of the outlet arm, so that the second male Luer cap and the female Luer cap at the distal end of the outlet arm can be screwed together to form a tight Luer lock, and wherein said second male Luer cap contains one or more tabs which will align with the one or more tabs on the outer surface of the female Luer cap at the distal end of the outlet arm, when the two Luer caps are screwed together, so as to achieve a desired configuration, with respect to each other, when the Luer caps are tightened together.

2. An improved rubidium-82 generator comprising:

a. a hollow column with a top portion, a middle portion and a bottom portion, said top portion including one or more notches, and a screen separating the middle portion and the bottom portion;

b. a top basket with one or more protrusions, said one or more protrusions configured to cooperate with the one or more notches in the top portion of the hollow column so as to cause the proper seating of the top basket in the top portion of the hollow column, said top basket further comprising a screen at its base and a side opening;

c. an inlet arm which intersects the hollow column at its top portion at a point where the inlet arm is aligned with the side opening in the top basket, and further wherein the inlet arm has a female Luer cap at its distal end, said female Luer cap containing one or more tabs on its outer surface;

d. an outlet arm which intersects but does not protrude into the hollow column at its bottom portion, wherein a notch is provided at the point of intersection on the bottom portion's inner surface, and further wherein the outlet arm has a female Luer cap at its distal end, said female Luer cap containing one or more tabs on its outer surface;

e. support means to support the inlet arm and the outlet arm to the hollow column;

wherein said hollow column, top basket, inlet arm, outlet arm and support means are constructed of a radiation resistant polypropylene;

f. a packing material comprising stannic oxide with strontium-82 adhered thereto, said packing material placed in the middle portion of the hollow column above the bottom screen and below the screen of the top basket;

g. a top stopper comprising a radiation resistant material, said top stopper configured to form a tight seal with the top portion of the hollow column but which does not block the inlet arm;

h. a bottom stopper comprising a radiation resistant material, said bottom stopper configured to form a tight seal with the bottom portion of the hollow column and minimizing a dead space in the bottom portion of the hollow column, without blocking the outlet arm;

i. a first crimp seal to crimp the top stopper to the top portion of the hollow column and a second crimp seal to crimp the bottom stopper to the bottom portion of the hollow column, wherein each crimp seal comprises steel with a thickness of about 0.2 mm and a central hole about 5.0 mm in diameter, wherein each crimp seal is crimped to a pressure of about 117 psi;

j. a first flexible tube comprising a flexible, radiation resistant polyvinyl chloride with a first male Luer cap comprising a rigid, radiation resistant polyvinyl chloride at one end of said first flexible tube, said first male Luer cap being configured to cooperate with the female Luer cap at the distal end of the inlet arm so that the first male Luer cap and the female Luer cap at the distal end of the inlet arm can be screwed together to form a tight Luer lock, and wherein said first male Luer cap contains one or more tabs on its outer surface which will overlap with the one or more tabs on the outer surface of the female Luer cap at the distal end of the inlet arm, when the two Luer caps are screwed together, the tabs overlapping, having been pushed past each other, to form a tight Luer lock which is resistant to inadvertent loosening; and k. a second flexible tube comprising a flexible, radiation resistant polyvinyl chloride with a second male Luer cap comprising a rigid, radiation resistant polyvinyl chloride at one end of said second flexible tube, said second male Luer cap being configured to cooperate with the female Luer cap at the distal end of the outlet arm so that the second male Luer cap and the female Luer cap at the distal end of the outlet arm can be screwed together to form a tight Luer lock, and wherein said second male Luer cap contains one or more tabs which will overlap with the one or more tabs on the female Luer cap at the distal end of the outlet arm, when the two Luer caps are screwed together, the tabs overlapping, having been pushed past each other, to form a tight Luer lock which is resistant to inadvertent loosening.

3. An improved rubidium-82 generator system comprising:

a. a rubidium-82 generator including an inlet arm and an outlet arm, and being surrounded by a generator shield;

b. a saline supply connected to the inlet arm of the rubidium-82 generator by one or more saline supply tubes connected to each other in series, said saline supply tubes being connected to each other and to the inlet arm of the rubidium-82, generator by a first connecting means;

c. one or more outflow tubes connected in series and connected to each other and to the outlet arm of the rubidium-82 generator via a second connecting means;

d. a divergence means at a terminal end of the outflow tubes, the divergence means being connected to a patient tube and a waste tube such that a liquid flowing through the divergence means can be diverted to the patient tube or the waste tube; and e. a waste bottle surrounded by a waste bottle shield, wherein the waste bottle is connected to the waste tube via a third connecting means;

wherein the improvements comprise:

f. support means to support the inlet arm and the outlet arm of the rubidium-82 generator; and g. the outlet arm intersects but does not protrude into a hollow column of the rubidium-82 generator at a bottom portion thereof, and a notch is provided in the hollow column at a point of intersection of the outlet arm and the hollow column.

4. The improved rubidium-82 generator system of claim 3, further comprising one or more additional tubes connected to each other in series and connected between the divergence means and the patient tube by a fourth connecting means, to provide for a desired distance from the rubidium-82 generator to a patient.

5. The improved rubidium-82 generator of claim 3, wherein each of the connecting means is a Luer connector.

6. The improved rubidium-82 generator system of claim 5, wherein the Luer connector comprises a female Luer cap and a male Luer cap, wherein one of said Luer caps contains a flange and the other of said Luer caps contains threads, configured so that the flange and threads cooperate with each other in such a way that the female Luer cap and male Luer cap can be screwed together, and wherein one or more tabs are provided on each of the male and female Luer caps, the tabs on the male Luer cap and the tabs on the female Luer cap achieving a desired configuration, with respect to each other, when the two Luer caps are tightened together.

7. The improved rubidium-82 generator system of claim 6, wherein the one or more tabs of each of the male and female Luer caps each comprise two tabs.

8. The improved rubidium-82 generator system of claim 6, wherein the desired configuration comprises each of the one or more tabs on the male Luer cap lining up with a corresponding tab of the one or more tabs on the female Luer cap.

9. The improved rubidium-82 generator of system of claim 6, wherein the desired configuration comprises each of the one or more tabs on the male Luer cap overlapping with a corresponding tab of the one or more tabs on the female Luer cap, thereby preventing over tightening or inadvertent loosening of the Luer lock.

10. The improved rubidium-82 generator system of claim 3, wherein the rubidium-82 generator, tubes, connecting means, divergence means and waste bottle are all constructed of radiation resistant materials.

11. The improved rubidium-82 generator system of claim 3, wherein the patient tube terminates in a check valve to prevent air from entering the patient tube when the patient tube is disconnected from the patient.

12. The improved rubidium-82 generator system of claim 11, wherein the check valve is constructed of radiation resistant materials.

13. The improved rubidium-82 generator system of claim 11, wherein the patient tube includes a sterile filter and the check valve is attached before the sterile filter.

14. The improved rubidium-82 generator system of claim 11, wherein the patient tube includes a sterile filter and the check valve is attached after the sterile filter.

* * * * *